United States Patent [19]

Patel

[11] Patent Number: 5,053,339
[45] Date of Patent: Oct. 1, 1991

[54] COLOR CHANGING DEVICE FOR MONITORING SHELF-LIFE OF A PERISHABLE PRODUCTS

[75] Inventor: Gordhanbhai Patel, Somerset, N.J.

[73] Assignee: J P Labs Inc., Piscataway, N.J.

[21] Appl. No.: 266,690

[22] Filed: Nov. 3, 1988

[51] Int. Cl.⁵ ............................................. G01N 31/22
[52] U.S. Cl. .......................................... 436/2; 116/206; 116/207; 116/216; 116/218; 252/408.1; 422/56; 422/57; 422/58; 426/88; 426/231; 436/7
[58] Field of Search ..................................... 422/56–58; 436/2, 7; 252/408.1; 116/206, 207, 216, 218; 426/88

[56] References Cited

U.S. PATENT DOCUMENTS

| | | |
|---|---|---|
| 2,614,430 | 10/1952 | Ballard et al. |
| 2,889,799 | 6/1959 | Korpman |
| 3,065,883 | 11/1962 | Gessler |
| 3,078,182 | 2/1963 | Crone et al. |
| 3,311,084 | 3/1967 | Edenbaum |
| 3,360,338 | 12/1967 | Edenbaum |
| 3,386,807 | 6/1968 | Edenbaum |
| 3,414,415 | 12/1968 | Broad, Jr. |
| 3,479,877 | 11/1969 | Allen et al. |
| 3,520,124 | 7/1970 | Myers |
| 3,677,088 | 7/1972 | Lang |
| 3,942,467 | 3/1976 | Witkonsky |
| 3,946,611 | 3/1976 | Larsson |
| 3,954,011 | 5/1976 | Manske |
| 3,967,579 | 6/1976 | Seiter |
| 3,981,683 | 9/1976 | Larsson et al. |
| 3,999,946 | 12/1976 | Patel et al. ............................ 422/56 |
| 4,042,336 | 8/1977 | Larsson |
| 4,057,020 | 11/1977 | Seiter |
| 4,154,107 | 5/1979 | Giezen et al. |
| 4,163,427 | 8/1979 | Cooperman et al. |
| 4,188,437 | 2/1980 | Ruhowetz |
| 4,195,056 | 3/1980 | Patel et al. |
| 4,195,058 | 3/1980 | Patel et al. |
| 4,212,153 | 7/1980 | Kydonieus et al. |
| 4,280,441 | 7/1981 | McNeely |
| 4,292,916 | 10/1981 | Bradley et al. |
| 4,382,700 | 5/1983 | Youngren |
| 4,410,493 | 10/1983 | Joslyn |
| 4,432,656 | 2/1984 | Allmendinger |
| 4,509,449 | 4/1985 | Chalmers |

FOREIGN PATENT DOCUMENTS 1521653  8/1978  United Kingdom .

Primary Examiner—Jill Johnston

[57] ABSTRACT

A color changing device for monitoring the time-temperature storage history, i.e. shelf life, of perishable products. The device is constructed of an activator tape, containing an activator composition matrix, an indicating tape, containing an indicating composition matrix and an optional barrier matrix between the activator tape and the indicating tape. At least one matrix is a pressure sensitive adhesive. The activating composition, e.g. an organic acid such as citric acid, diffuses through the barrier and/or indicating matrix to continuously contact the indicating composition, e.g. an acid-base dye indicator such as 2,2',4,4',4''-pentamethoxy triphenylmethanol, to produce a visually observable color change at the temperature being monitored. The color intensifies with time and temperature, as more activator composition diffuses into the indicating matrix. The matrices are water-impermeable and the device preferably possesses activation energy and rate constant values for the color change which are substantially the same as those for product decay. This allows accurate and continuously observable monitoring of the abailable shelf-life of the perishable product to which the device is adhered to.

18 Claims, 7 Drawing Sheets

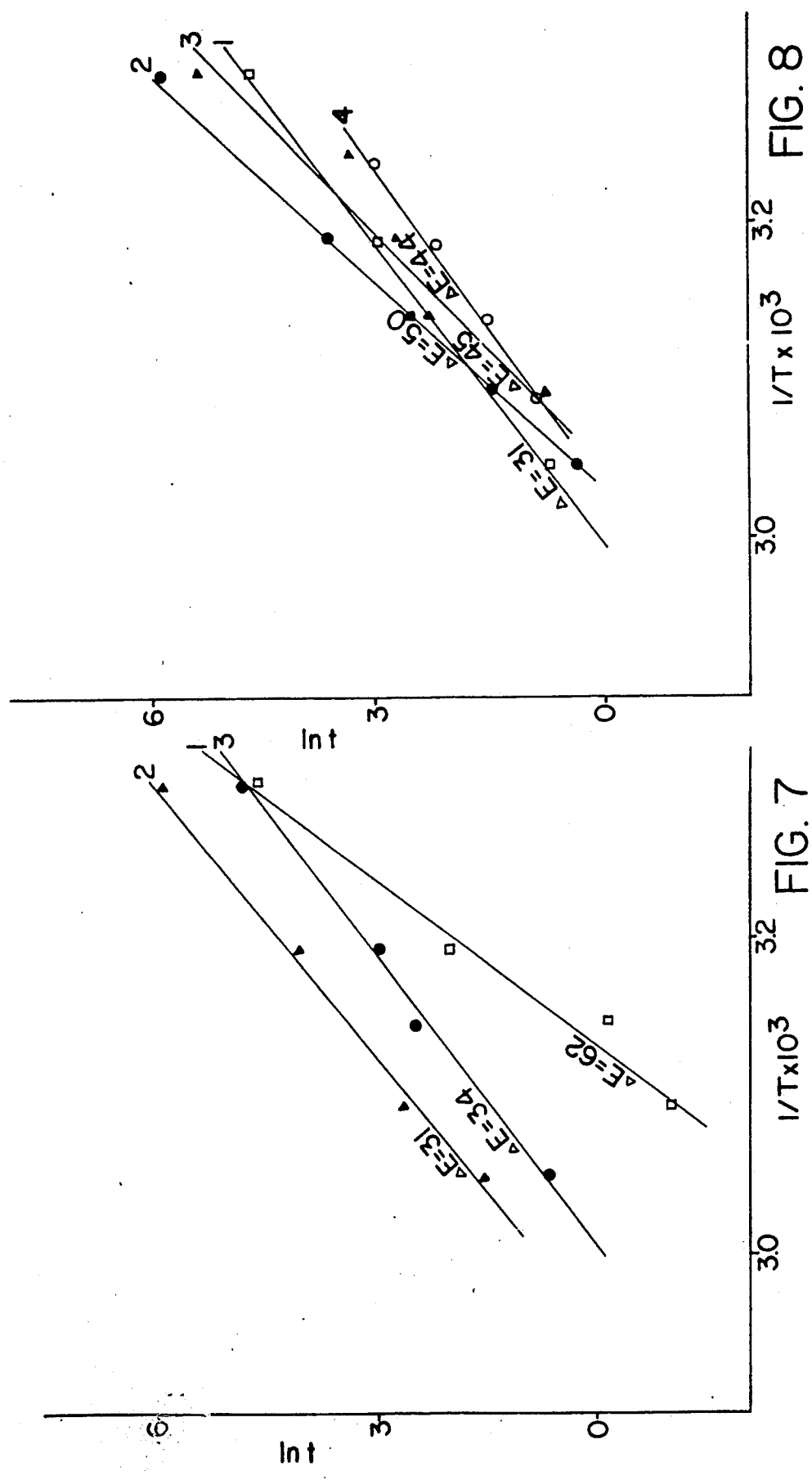

COLOR CHANGING DEVICE FOR MONITORING SHELF-LIFE OF A PERISHABLE PRODUCTS

This invention was supported in part by a grant (#86-SBIR-8-0109) from the U.S. Department of Agriculture, under the Small Business Innovation Research (SBIR) Program.

BACKGROUND OF THE INVENTION

1. Field of the Invention

This invention relates to a color changing time-temperature history device for measuring the shelf-life of perishable products. The device is constructed of an activating tape, containing an activator composition in a matrix and an indicating tape, containing an indicating composition in a matrix. At least one of the matrices, is being a pressure sensitive adhesive. The device may optionally contain a barrier, preferably a pressure sensitive adhesive, between the activating tape and the indicating tape.

2. Brief Description of the Prior Art

Perishable products have measurable shelf-lives, which are usually expressed within specified limits as the time left for available end use. By the term "perishable products" is meant to include perishable foods having a measurable shelf life such as fresh, refrigerated, and frozen, vegetables, fruits, meats, fish, poultry, dairy products, bakery products, juices, pre-cooked foods, soft and alcoholic beverages, and also including nonfood items having extended shelf lives ranging from a few hours to some years including pharmaceuticals, vaccines, sera, blood, blood plasma, cosmetics, reactive chemical compounds, biochemical products, batteries, x-ray film and photographic films. For example, FIG. 2 shows the shelf lives of various perishable products plotted in natural logarithm of shelf life in months against reciprocal of absolute temperature resulting in straight line graphs. For example from the graph, it can be seen that Eact's for corn cereal and strawberry are 13.5 and 44.0 kcal/mole. The shelf lives for frozen asparagus, poultry and strawberry at 180° C. are 180, 360 and 630 days respectively.

A quantitative view of hypothetical product decay rates is seen in FIG. 1. In general, by plotting the natural logarithm of the shelf life or decay rate of product versus the reciprocal of the absolute temperature (1/T in degrees Kelvin) a straight line is generally obtained defining the temperature sensitivity characteristics of product decay. The slope of the line is referred to as Eact.,(or E) the energy of activation of the product decay and the ordinate intercept (Y intercept) is a constant for the decay process. The same straight line graph can be used to illustrate the rate characteristics for the color change of a device.

The well-known Arrhenius equation describes the characteristics of the above-described straight line produced in FIG. 1:

$$\ln k = A - Eact/RT$$

where, ln k = natural logarithm of the reaction rate
A = pre-exponent constant, also referred to as the rate constant
Eact = activation energy
R = universal gas constant
A = absolute temperature in degrees Kelvin.

FIG. 1 also illustrates difficulties involved in the use of a time-temperature history indicator device which undergoes an observable color change to monitor the shelf life of the perishable product at different temperatures. If the perishable product decay is line B and the indicator device is line A, then at Ti, it is seen that the product decay and rate of color change of the indicator are identical and thus the indicator will accurately monitor the shelf life of the perishable product at this temperature.

However, a problem arises if the perishable is stored at the higher temperature Th. In this case, the indicator A will undergo color change prior to expiration of the usable shelf life of the product thus causing the product to be prematurely discarded. Conversely, if the perishable is stored at lower temperature Tl, the shelf life of the product will expire prior to the termination of the color change of the indicator, a potentially dangerous situation for those perishables which for example, can become contaminated with harmful bacteria, e.g. botulism. As is seen in FIG. 1, the problem with using the indicator A, to monitor the shelf life of perishable B, is that the slopes of the lines. i.e. energies of activation, are not identical in the temperature region of measurement.

Further, assuming that line C is the indicator and line B the perishable, it is seen that the two lines are parallel and have identical Eact's. However, since the rate constant (Y intercept) for C is much lower than that for B, monitoring the shelf of the perishable B at any temperature, will result in the indicator changing color at a significantly earlier time prior to the end of the shelf life, resulting in a premature rejection of the product. The problem here is that even though the Eact for product decay and indicator color change are identical, the rate constants for the two processes are different and thus lead to erroneous shelf life monitoring.

Thus, in order to be an effective indicator for monitoring the shelf life of perishable product, the characteristics of the indicator versus the product must be such that preferably both the Eact and rate constant of the color change are substantially identical to those of product decay of the perishable product, i.e. they both exhibit substantially identical Arrhenius graphs in the temperature region of measurement.

Further, it is highly desirable as in the case of perishables having a relatively short shelf-life, i.e. milk, fish, eggs, and ice cream, to be continuously aware of the remaining shelf-life of a perishable product so that contingencies can be made for their disposal, rather than be confronted with an unexpected abrupt color change signifying termination. It is also desired that the device be in a form which is easily manufactured and readily applied and adhered to the perishable, such as a "tape" device. Thus, what is highly desired in the art is a monitoring device preferably affixed to a perishable as a "tape", which accurately illustrates the remaining shelf life of the perishable.

A large number of devices have been reported in the patent literature for monitoring thermal degradation of perishables.

For example, several patents describe time-temperature monitoring (TTM) devices based on diffusion of liquids, vapors or gases through a barrier film. For example, in U.S. Pat. Nos. 4,195,056 and 4,195,058, G. N. Patel describes a device based on diffusion of vapor through a barrier film to introduce color change in the indicator on the other side of the barrier. In order to prevent escape of the vapor, the device is sealed in a plastic container and requires a solvent reservoir.

A somewhat similar device is described by Giezen et al in U.S. Pat. No. 4,154,107. The device utilizes an activator acid in a pressure sensitive adhesive which migrates to contact an organic dye producing an aqueous-mediated color change. The preferred device also requires an absorbant paper element to contain the indicator and a wetting agent to retain water to introduce color change. The activating/indicating components used in the device are water soluble and hence the performance of the device is adversely affected by moisture and humidity. In order to protect the device, an enveloping plastic film is employed.

Kydonieus et al in U.S. Pat. No. 4,212,153 describe a device for monitoring product shelf life in which a dye preferably migrates from a lower plastisol layer to an upper indicator layer, being preferably polyvinylchloride. The device can also utilize a barrier film to introduce an induction period to color change, but doesn't describe a tape device, or the separate use of an activator and indicator agent.

Bradley et al in U.S. Pat. No. 4,292,916 describe a tape device for monitoring shelf life which involves the migration of a dye from a carrier layer to a transfer layer to highlight a message. However, the device preferably uses a porous barrier such as cheese cloth, requires a protective cover, does not describe the use of pressure sensitive adhesives to bond the different layers of the device together and requires an impervious covering layer for the entire indicator device.

U.S. Pat. No. 3,520,124 to Myers describes a device to indicate a predetermined time interval based on two or more materials which react, either chemically or physically over a predetermined period to produce a termination signal. The reacting materials are carried on a base member and are separated by a barrier preventing contact. Upon elimination of the barrier, a commencement signal is produced indicating the time reaction is underway. However, there is not described a tape device or the use of pressure sensitive adhesives for bonding the layers of the device together.

Other patents in the art include: U.S. Pat. Nos. 3,677,088; 3,967,579; 3,360,338; 4,057,029; 3,065,083; 4,188,437; 2,889,799; 3,078,182; 3,311,084; 3,386,807; 4,154,107.

Also described in the art are "moving boundary" devices which operate on the principle of a moving band of produced color so that the continuously elapsed time of the monitored period can be visually observed. They are described in U.S. Pat. Nos. 4,382,700; 4,196,057; 4,196,055; 4,432,656; 2,614,430; 3,479,877; 3,414,415; 3,942,467; 3,954,011; 3,981,683; 4,057,029; 4,163,427; 4,280,441; 4,410,493; 4,509,449.

Many of the above referred-to devices use liquids or vapors as the activator in the color-indicating systems rather than a solid water-impermeable material which is required in a tape. Further the references do not specifically teach one skilled in the art how to design a particular tape device in order to match the product decay characteristics particularly with respect to the Eact and the rate constant to accurately monitor the perishable product over a range of storage temperature conditions.

SUMMARY OF THE INVENTION

We have found that an accurate color changing device for measuring the time-temperature history and remaining shelf-life of a perishable product can be constructed by matching the product decay Arrhenius characteristics with the color change Arrhenius characteristics of the indicator. This is done by employing an activator-indicator system in which the activator and indicator are separately contained in matrix layers, optionally employing a barrier matrix layer, which are sandwiched together by means of at least one pressure sensitive adhesive and which allow the migration of the activator through the barrier and/or indicator matrix. The diffused activator reacts with the indicator to produce a color change. The rate of color production is selected to match the product decay rate in the temperature range of interest, generally being the storage temperature. This is done by selecting the matrix layers and optionally the barrier layer to produce an activator-indicator system that exhibits the same slope, i.e. activation energy, and apparent extrapolated rate constant, i.e. Y-intercept, in the desired temperature range. By use of this technique, color changing devices can be constructed to monitor a wide range of perishable products and particularly including foods which are susceptible to thermal degradation.

By this invention there is provided a device for monitoring the time-temperature storage history of a perishable product having a measurable activation energy of product deterioration comprising:

a) an indicator tape comprised of a transparent polymer film and affixed thereto at least one water-impermeable matrix layer containing an indicator composition:

b) an activator tape comprised of a substrate and affixed thereto at least one water-impermeable matrix layer containing, in solid solution, an activator composition:

c) a composite barrier matrix, said indicator tape and activator tape matrix layers, bonded together by at least one pressure sensitive adhesive; said activator composition being capable of diffusing through said composite matrix in a predetermined time to contact said indicator composition producing a visually observable color change in said indicator composition; said device being substantially impermeable to moisture, and said device possessing an activation energy and rate constant for color change which are substantially the same as the activation energy and rate constant for product deterioration of the perishable product in the temperature region of monitoring.

One of the simplest form of the color changing device is shon schematically in FIG. 3, wherein said indicator tape matrix layer (a) and said activator tape matrix layer (b) are adhered together to form a uniform thickness composite matrix (c).

In order to introduce an induction period for the color change and vary the activation energy, a barrier matrix layer of uniform thickness can be placed between both matrix layers as shown schematically in FIG. 4.

Alternatively, the barrier layer of uniform thickness can be coated on the indicating matrix as shown schematically in FIG. 5.

In order to prevent, migration of the indicator, the barrier layer should, preferably, be essentially impermeable to the indicating composition. The matrix of the barrier layer could be the same as that of indicating or activating layer, or could be an entirely different matrix.

Another embodiment is where the device is characterized in having an activation energy and rate constant of color change which is substantially the same as the activation energy and rate constant for product decay of the perishable product in the temperature region of monitoring.

Also provided is a process for measuring the shelf life of a perishable product comprising the step of affixing to said product the device described above and activating the device.

Further provided is a perishable product having the device described herein, in inactivated or activated form, attached thereto.

Still further provided is a process for constructing the device described herein for measuring the shelf life of a perishable product comprising the step of laminating:

a) an indicator tape comprised of a transparent polymer film and affixed thereto, at least one matrix layer containing an indicator composition; and b) an activator tape comprised of a substrate and affixed thereto at least one matrix layer containing an activator composition in solid solution; producing a composite matrix layer wherein said activator being capable of permeating through said barrier at a predetermined time to contact said indicator producing a visually observable color change in the indicator tape.

Also provided is the above-described device which is activated by thermal annealing, ultraviolet radiation or applied pressure.

Furthermore there is provided a device for measuring the shelf-life of a perishable product having a measurable activation energy of product deterioration comprising:

a) an indicator tape comprised of a transparent polymer film and affixed thereto at least one water-impermeable matrix layer containing an indicator composition:

b) an activator tape comprised of a substrate and affixed thereto at least one water-impermeable matrix layer containing in solid solution an activator composition:

c) a composite matrix, comprised of a plurality of laminated matrix layers, including said indicator tape and activator tape matrix layers, bonded together by at least one pressure sensitive adhesive, and said activator composition is capable of diffusing through said composite matrix in a predetermined time to contact said indicator composition producing a visually observable change in predetermined time in fluorescence of said indicator composition.

Also provided is a device for measuring the shelf-life of a perishable product having a measurable activation energy of product deterioration comprising:

a) an indicator tape comprised of a transparent polymer film and affixed thereto at least one water-impermeable matrix layer containing an indicator composition:

b) an activator tape comprised of a substrate and affixed thereto at least one water-impermeable matrix layer containing in solid solution an activator composition:

c) a composite matrix, comprised of a plurality of laminated matrix layers, including said indicator tape and activator tape matrix layers, bonded together by at least one pressure sensitive adhesive, and said activator composition is capable of diffusing through said composite matrix in a predetermined time to contact said indicator composition producing a measurable change in the electrical conductance of said indicator composition.

There is furthermore provided a device for monitoring the time-temperature storage history of a perishable product having a measurable activation energy of product deterioration comprising:

a) an indicator tape comprised of a transparent polymer film and affixed thereto at least one water-impermeable matrix layer containing an indicator composition positioned below an opaque additive:

b) an activator tape comprised of a substrate and affixed thereto at least one water-impermeable matrix layer containing in solid solution an activator composition capable of dissolving said opaque additive:

c) a composite matrix, comprised of a plurality of laminated matrix layers, including said indicator tape and activator tape matrix layers, bonded together by at least one pressure sensitive adhesive, and said activator composition is capable of diffusing through said composite matrix in a predetermined time to contact and dissolve said opaque additive, producing a visually observable change in said indicator composition.

Further there is provided a process for altering the activation energy of the above-described device to match that of the perishable product comprising the step of varying the nature of one of the following components of the device selected from: activator matrix, indicator matrix, barrier matrix, activator, indicator, additives in a matrix, interface between two matrices, the degree of crystallinity of a given matrix, or combination of said components.

DESCRIPTION OF THE FIGURES

FIG. 3 is a schematic cross sectional view of a two-layer device in which:

Figure 1:
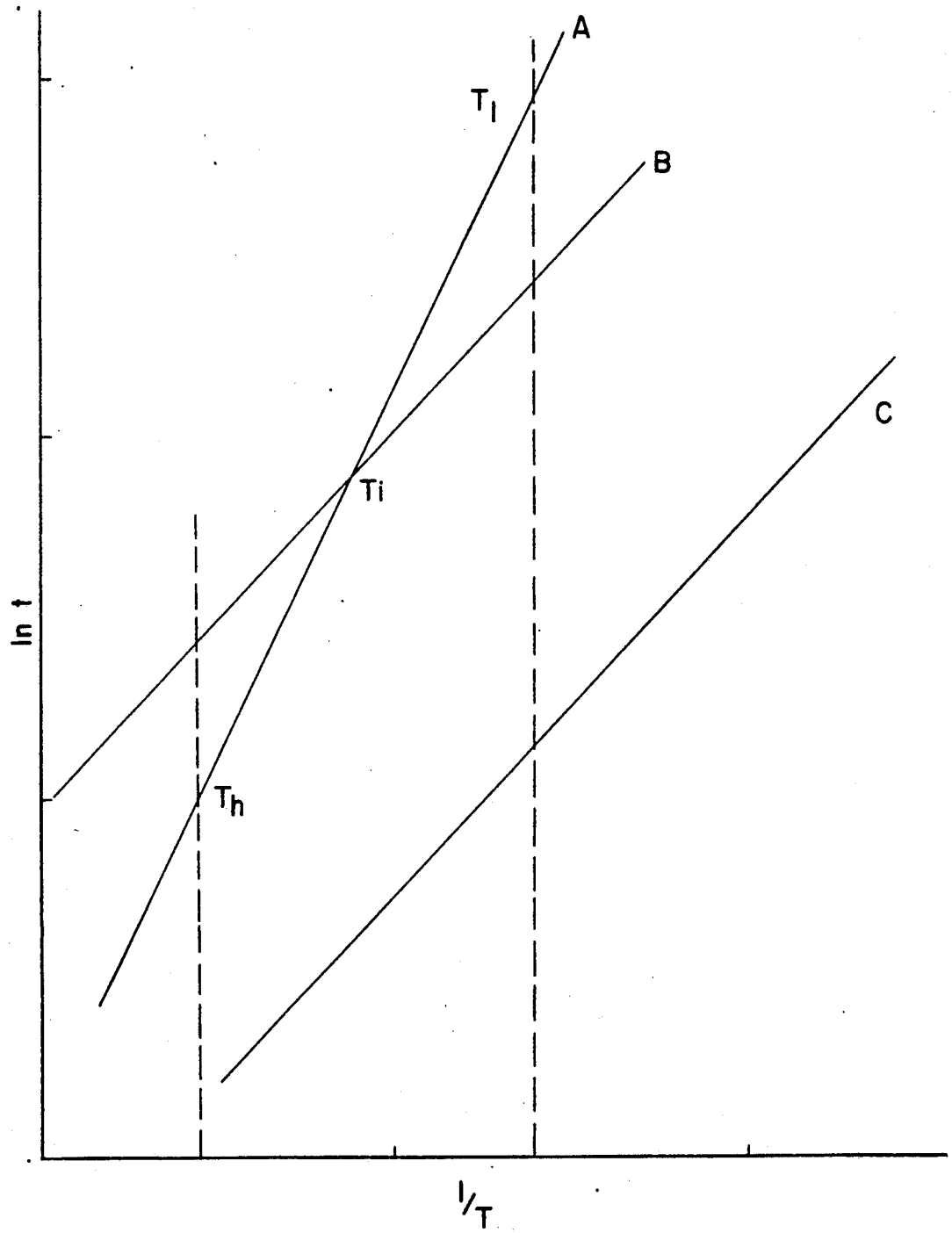
FIG. 1 illustrates a hypothetical Arrhenius kinetics diagram for a perishable B and indicator A being non-parallel (different Eact's) but having a common process rate at Ti, and indicator C being parallel to B (same Eact's) but with no common reaction rate constant.

(a) is the indicator tape comprised of plastic film 1, having a uniform thickness matrix layer 9, containing indicator 3;

(b) is the activator tape comprised of plastic film 4, having a uniformed thickness matrix layer 10, containing activator 6 in solid solution and an adhesive layer 7;

(c) is the activated device obtained by the lamination of the indicator matrix onto the activator matrix forming the composite matrix.

FIG. 4 is a schematic cross sectional view of a three-layer device containing a barrier layer matrix of uniform thickness in which:

(a) is the indicator tape comprised of plastic film 1, having an adhered matrix layer 2, containing indicator 3;

(b) is the barrier matrix layer 11 of uniform thickness;

(c) is the activator tape comprised of plastic film 4, having a uniform thickness matrix layer, 10 containing activator 6 in solid solution and an adhesive layer 7;

(d) is the activated device obtained by laminating the barrier matrix layer between the indicator tape and activator tape matrices.

Figure 5A:
Figure 5B:
Figure 5C:
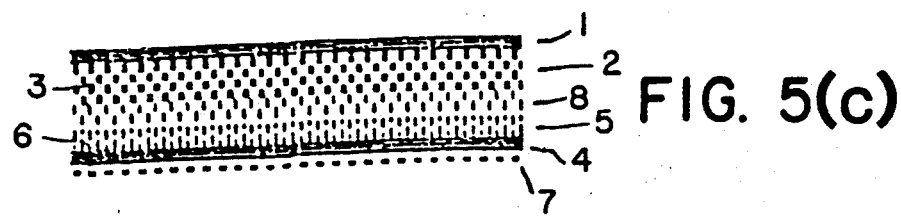

FIG. 5 is a schematic cross sectional view of another embodiment of a three-layer device employing a uniform thickness middle barrier matrix layer applied on the activator tape in which:

(a) is the indicator tape comprised of plastic film 1, having a matrix layer 2, containing indicator 3, and an attached, laminated, uniform thickness barrier layer matrix 8;

(b) is the activator tape comprised of plastic film 4, having a matrix layer 5, containing activator 6 in solid solution, and an adhesive layer 7;

(c) is the activated device obtained by lamination of the indicator matrix (and the barrier matrix) onto the activator matrix.

Figure 6:
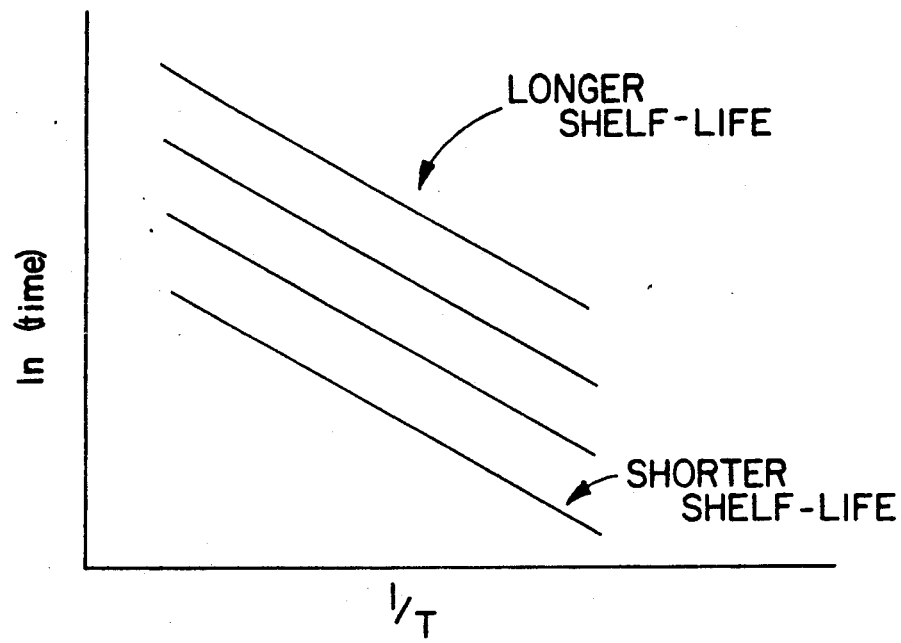
Figure 6:
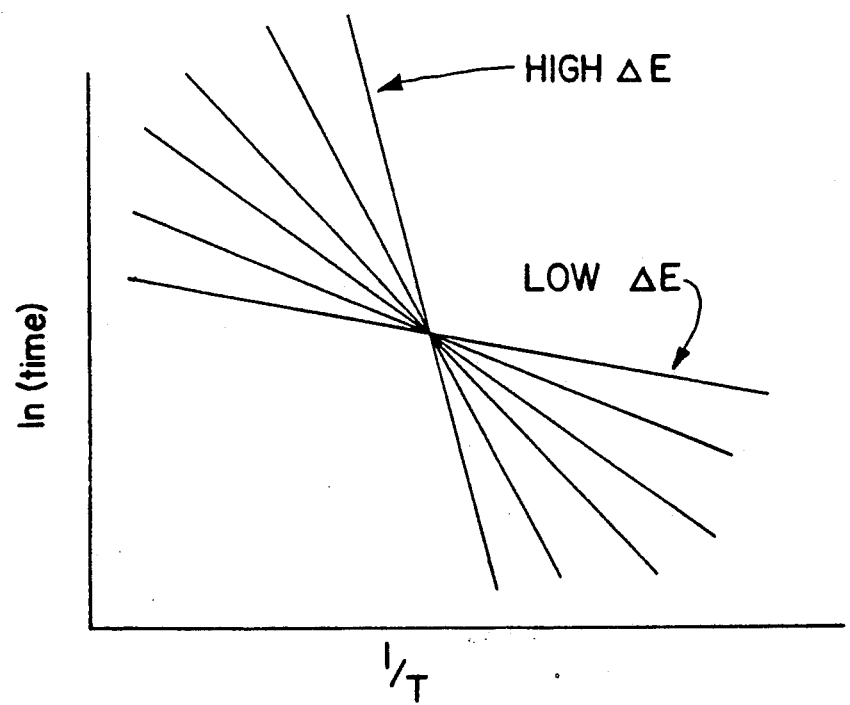

FIG. 6 is an Arrhenius kinetic diagrams:

(a) showing the variation in the rate constants of hypothetical devices having the same activation energy;

(b) showing the variation in the activation energies of hypothetical devices.

FIGS. 7–12 illustrate the alteration of the activation energy in athe invention device by suitable changes in the nature of the individual components.

BRIEF DESCRIPTION OF THE INVENTION AND PREFERRED EMBODIMENTS

Figure 3A:
Figure 3B:

The device can best be described by reference to the Figures. Referring to FIG. 3, substrate 1, a piece of transparent plastic film, is coated with a matrix 9 such as an adhesive, containing a known concentration of an indicator 3. This tape of FIG. 3a is referred hereafter to as the "INDICATOR TAPE". Similarly, substrate 4, a flexible substrate, is coated with a matrix 10, containing an activator 6, in solid solution, as shown schematically in FIG. 3b. By the term "solid solution" is meant that the activator is completely dissolved and uniformly dissolved/dispersed throughout the activator matrix layer. This tape of FIG. 3b is referred hereafter to as "ACTIVATOR TAPE". The matrices 9, and 10 can be the same or different. Both matrices must be water-impermeable and one of the matrices should preferably be a pressure sensitive adhesive and have an ability to form an adhesive bond with the other matrix.

If both the substrates, 1 and 4, are transparent, either one of them can be applied to perishable container. The substrate contacting the perishable container is referred to hereinafter as the base substrate or base film and is preferably the activator substrate. The base film may preferably have another adhesive backing 7, so that the device can be applied to a perishable container. The adhesive 7 does not contain an activator or indicator. The activator film 4 can be transparent or opaque (e.g. metal foil) but the top (indicator) film 1 must be transparent, so that the color change can be visually observed. When the activator reacts with the indicator, it produces a visually observable color change, which is essentially simultaneously over the surface of the indicator, unless the indicator is in the form of a bar code or alphanumeric symbol.

Figure 3C:
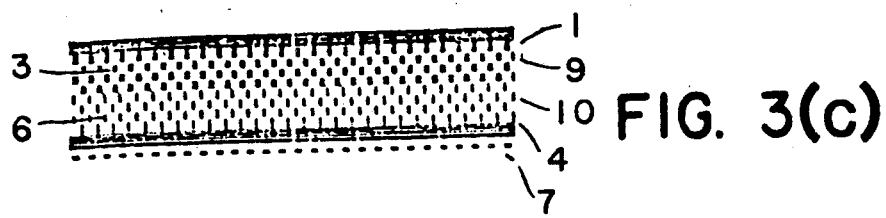
Figure 4A:
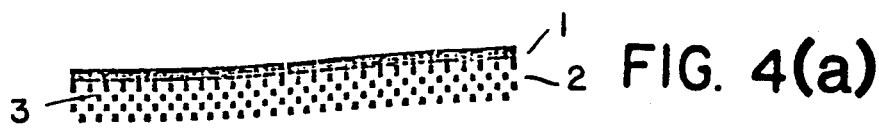
Figure 4B:
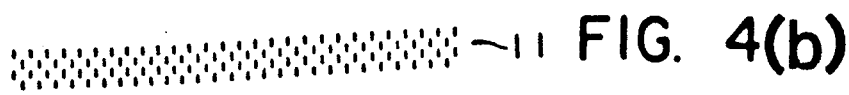
Figure 4C:
Figure 4D:
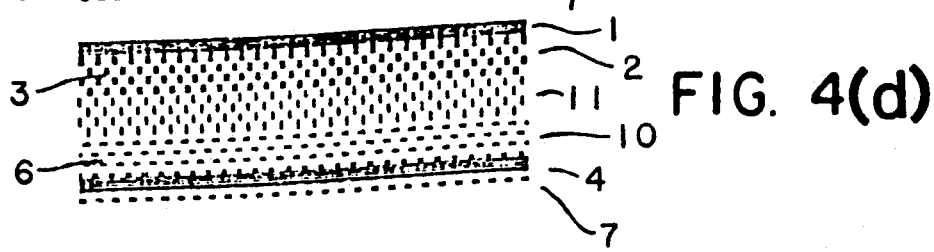

The device is activated by laminating the indicator tape to the activator tape so that the indicator matrix contacts the activator matrix as shown in FIG. 3c. As one of the matrices is an adhesive, e.g. pressure sensitive adhesive, a moderately applied pressure will form an effective bond between them. Once the device is activated, the two matrix layers form a composite layer (film). The term "ACTIVATION" is used to describe the process of adhering indicator tape of FIG. 3a to the activator tape of FIG. 3b to form the reactive (color changing) device of FIG. 3c, which is referred hereinafter to as "TAPE DEVICE".

Once the device is activated, the solid solution activator 6 will migrate into the indicator matrix 9, where it will react with the indicator 3 and introduce a color change. The indicator display can be a printed message.

The color changing device of the instant invention can have many modifications and embodiments, which are presented below:

The three layer device of FIG. 5 is comprised of three parts, the indicator tape (a), the activator tape (b), and a barrier matrix layer 8, adhered to the indicator tape. The barrier matrix layer can be applied to either indicator or activator tape to form the composite matrix at the time of activation for end use. A transparent plastic film 1, is coated with the matrix medium 2, containing a known concentration of an indicator 3 adhered to the barrier matrix 8, as shown schematically in FIG. 5a to form the indicator tape. Similarly, a piece of flexible substrate 4, is coated with an matrix 5, containing an activator 6, in solid solution, as shown in FIG. 5b to form the activator tape. This tape is similar to that shown in FIG. 3b. The barrier layer 8 can be coated onto matrix 5 as well. The matrices 2, 5 and 8 can be of the same or different compositions, and preferably at least one is a pressure sensitive adhesive. The base film 4 may have another adhesive backing 7, so that the device can be applied to a perishable container. The device is activated by laminating the indicator tape onto the activator tape as shown in FIG. 5-C. Once the device is activated, the three layers form a composite layer. The activator will diffuse through the barrier matrix into the indicator matrix where it will react with the indicator and introduce a color change.

Alternatively, the barrier layer of uniform thickness matrix of different permeabilities can be coated on the indicator matrix as shown in FIG. 4. Thus the three layer device becomes two layer device.

Another modification of the device of either FIGS. 3–5 is to coat or print the indicator in form of message. Instead of the continuous coating of the indicator, one can coat or print the indicator in form of a message, e.g. IF THIS IS RED, DO NOT USE. In such case, only the message will gradually appear or undergo the color change.

Another modification of the basic device is to coat or print the indicator in form of bar codes. Instead of the continuous coating of the indicator, one can coat or print the indicator in form a of bar code. In this case, only the bars will undergo the color change and a conventional bar code reading apparatus can be used to read shelf life of the perishable. Other product information, such as inventory control, can also be combined into the bar codes.

The device can also be prepared and activated on perishable production line. For example, perishable containers can be printed with an indicator. The coating (layer) of activator can be applied at the time of top coating to activate the device at the time of filling the container with the perishable.

The indicator tape and activator tape can be prepared in the form of big rolls and stored separately essentially indefinitely. The rolls can subsequently be loaded onto a particular processing machine/equipment. In order to activate the device, the rolls will laminate the activator tape onto the indicator tape (with a barrier film in between if required), cut to the desired size and applied to the perishable. Commercially available equipment for lamination and application of labels which are conventional can be combined and modified for activation and application of the device on line.

The size of the device can be as small as a few millimeters to several centimeters or larger, if desired. The thickness of the device typically can be from a thousandth of a centimeter to a millimeter, or thicker, if desired.

The indicator and activation tapes can be prepared by coating the mixture of indicator (and activator) and matrix on a substrate. Coating is an old and well developed technology. A variety of processes/equipment have been developed for coating adhesives, inks, laquers, and other polymeric materials. Common coating methods are: air knife, brush, calender, cast coating, curtain, dip, extrusion, blade, floating knife, gravure, kiss roll, off-set, reverse roll, rod, spray, and squeeze roll. These methods have been reviewed by Coeling, and Bublick (K. J. Coeling, and T. J. Bublick, Encycl. Polym. Sci. Eng., Vol. 3, 552–615, 1986). Most of the above methods can be used for coating the matrix on a wide range of base materials.

The device can be activated by lamination of the activator tape with the indicator tape. Lamination is a process of uniting two or more layers of different or similar materials into one composite layer by the action of heat or pressure. Since one of the substrates is coated with an adhesive, preferably a pressure sensitive adhesive, it can be laminated with the other substrate by application of moderate pressure, or heat. In a perishable product, packaging plant, the devices can be activated by lamination and applied directly onto the containers.

The device can be printed in form of bar codes. "Bar coding" is used to track inventory in the warehouses and to read prices of foods in supermarkets. Bar coding is a technique for automated data collection. A bar code is a series of black bars and spaces which represent letters and/or numerals. (See P. E. Boyle, Barcode News, November 1985). To decode the information in a bar code, a small spot of light is passed over the bars and spaces via a scanning device. The bar code will reflect the light back into the scanner in various amounts. These differences in reflections are translated into electrical signals by a light detector inside the scanner. The signals are converted into binary zeroes and ones which are used in various combinations to stand for specific numbers and letters.

The basic components of the device and their functions are described below:

The indicator film 1 can be any transparent plastic film being water impermeable on which a matrix such as an adhesive or ink can be coated. It should preferably be clear in order to observe the color change of the indicator. Representative examples include a large number of plastic films including those made from polyethylene, polypropylene, cellulose derivatives such as cellulose acetate, polyesters such as poly(ethylene terephthalate), polyamides such as nylon-66, polyurethanes, polyvinylchloride, and polycarbonates such as poly(bisphenol-A carbonate). Preferred indicator films are polyethylene, polypropylene, cellulose acetate, poly(ethylene terephthalate), polyvinylchloride and multilayer laminated films, preferably comprising a composite of polyethylene, polyethylene terephthalate and polyvinylchloride.

The activator tape base film 4 can be any transparent or opaque plastic film or metal foil being water-impermeable on which a matrix such as an adhesive can be coated on both the sides. Once the device is assembled, this tape is applied to the perishable container. Aluminium foil and the plastic films listed above for the indicator film can be used.

Preferred activator films are aluminum, polyethylene, polypropylene, cellulose acetate, poly(ethylene terephthalate), polyvinylchloride and multilayer laminated films, preferably comprising the composite described above.

The indicator, activator and barrier layer matrix materials can be any water-impermeable polymeric material suitable for incorporating a variety of inks, paints or adhesives which are preferably transparent and in which an activator and indicator can be incorporated. At least one matrix is preferably a pressure sensitive adhesive. General classes of polymers suitable for activator and indicator matrix include resins such as epoxy, phenol-formaldehyde, amino-formaldehyde, polyamides, vinyls, acrylics, polyurethanes, polyesters, water soluble resins, alkyds, elastomers, and rosins. Some of them are listed in the following references, "Resins for Surface Coatings", P. Oldring and G. Hayward, and "Resins and Varnishes for Ink and Paint", both published by McNair Publications, New York, N.Y.

Pressure sensitive adhesives (see "Handbook of Pressure Sensitive Adhesives Technology" by Don Schar (Ed,), Van Nostrand N.Y., 1982) are a preferred matrix layer. Included are pressure sensitive adhesives having an elastomer or rubbery polymer as the elastic component and a low molecular weight tackifying viscous component. Common rubber based pressure sensitive adhesives include natural elastomers, synthetic elastomers such as polychloroprene, polyurethane, and random and block copolymers of styrene-butadiene, styrene-isoprene, polyisobutylene, butyl rubber, and amorphous polypropylene. These are compounded with tackifying resins to formulate hot melt pressure sensitive adhesives. Common acrylic adhesives such as polymers of 2-ethylhexylacrylate, butyl acrylate, ethylacrylate, and acrylic acid. These acrylic adhesives are inherently pressure sensitive. Polymers and copolymers of vinyl ethers such as vinylmethylether, vinylethylether and vinylisopropylethers are used as pressure sensitive adhesives. Two types of silicone gums; 1) all methyl based and 2) the phenyl modified can also be used as pressure sensitive adhesives. The silicone resin is used as a tackifier and by adjusting the resin to gum ratio, they can be made with a wide range of adhesion properties. High silicone gum content adhesives are extremely tacky. Silicone adhesives are also crosslinked (cured) by catalysts such as benzoyl peroxide and amino silane.

In order to print a bar code or message, an ink form of the matrix is more convenient than an adhesive. Useful herein are a variety of inks such as flexo, gravure, off-set, letter press, and litho which are used for printing. Inks are composed of three basic components, vehicle (solvent), pigment (color) and binder (polymer). The ink (matrix) for the device can be composed of the similar three basic ingredients, indicator (pigment), solvent (vehicle) and matrix (binder) such as cellulose nitrate, rosin esters, acrylate and vinyl polymers, polyesters, polyamides and polyepoxy.

The barrier layer material for devices of FIGS. 4–5, as described above, can be any polymeric material in which the activator can diffuse through, but inhibits any significant diffusion by the indicator. The barrier material can be an adhesive, ink or a plastic film as described above.

Preferred barrier materials are polyethylene, polypropylene, cellulose acetate, poly(ethylene terephthalate), polyvinylchloride, epoxy, phenol-formaldehyde, amino-formaldehyde, polyamides, vinyls, acrylics, polyurethanes, polyesters, silicone resins, water soluble resins, alkyds, synthetic and natural elastomers, and rosins.

The function of the barrier matrix layer is twofold, to increase the time for color change, i.e., rate constant, and also to alter the activation energy of the device.

The activator-indicator compositions can be any two compounds which interact by a physical or chemical reaction to produce an observable color change or measurable physical characteristic. The activator and indicator can be solid or liquid. The activator should dissolve in, i.e. form a solid solution with, its matrix and must be able to migrate out of the activator matrix. The indicator and activator can be one compound or a mixture of two or more compounds including catalyst or reaction medium.

A large number of reactions are associated with color changes. In each type of color changing reaction there are several classes of compounds and each such class has several compounds which undergo a color change. Below are some type of reactions and classes of compounds which can be used as indicators and activators in the invention device.

Color changing reactions and indicators are used for detection and monitoring of organic, inorganic and organometallic compounds. Such color changing reactions and compounds are listed in a large number of books, reviews and publications, including those listed in the following references: Justus G. Kirchner, "Detection of colorless compounds", Thin Layer Chromatography, John Wiley & Sons, New York, 1976; E. Jungreis and L. Ben. Dor., "Organic Spot Test Analysis", Comprehensive Analytical Chemistry, Vol. X, 1980; B. S. Furniss, A. J. Hannaford, V. Rogers, P. W. Smith and A. R. Tatchell, Vogel's Textbook of Practical Organic Chemistry, Longman London and New York, p. 1063-1087, 1986; Nicholas D. Cheronis, Techniques of Organic Chemistry, Micro and Semimicro Methods, Interscience Publishers, Inc. New York, 1954, Vol. VI, p. 447-478; Henry Freiser, Treatise on Analytical Chemistry, John Wiley and Sons, New York-Chinchester-Brisbane-Toronto-Singapore, 1983, Vol. 3, p. 397-568; Indicators, E. Bishop (Ed.), Pergamon Press, Oxford, U.K., 1972. These reactions and compounds can be used in the device for recording time-temperature history. Listed below are representative classes of reactions and compounds that can be used in the device.

Oxidizing agents can oxidize reduced dyes and introduce a color change. Similarly, reducing agents can reduce oxidized dyes and introduce a color change. For example, ammonium persulfate can oxidize colorless leucocrystal violet to violet colored crystal violet. Reducing agents such as sodium sulfite can reduce crystal violet to leucocrystal violet. Thus oxidizing and reducing agents can be used as activators with appropriate redox indicators, in the invention device.

Representative common oxidants (oxidising agents) include: ammonium persulfate, potassium permanganate, potassium dichromate, potassium chlorate, potassium bromate, potassium iodate, sodium hypochlorite, nitric acid, chlorine, bromine, iodine, cerium(IV) sulfate, iron(III) chloride, hydrogen peroxide, manganese dioxide, sodium bismuthate, sodium peroxide, and oxygen. Representative common reducing agents include: Sodium sulfite, sodium arsenate, sodium thiosulfate, sulphurous acid, sodium thiosulphate, hydrogen sulfide, hydrogen iodide, stannous chloride, certain metals e.g. zinc, hydrogen, ferrous(II) sulfate or any iron(II) salt, titanium(III) sulphate, tin(II) chloride, tin(II) chloride and oxalic acid. The following table provides some representative preferred oxidation-reduction indicator combinations and their respective color changes:

TABLE 1

Representative oxidation reduction indicators and their color changes.

| Indicator | Color change | |
|---|---|---|
| | Oxidized form | Reduced form |
| 5-Nitro-1,10-phenanthroline iron(II) sulphate (nitroferroin) | Pale blue | Red |
| 1,10-Phenanthroline iron(II) sulphate(ferroin) | Pale blue | Red |
| 2,2'-Bipyridyl iron(II) sulphate | Faint blue | Red |
| 5,6-Dimethylferroin | Pale blue | Red |
| N-phenylanthranilic acid, | Purple red | Colorless |
| 4,7-Dimethyl-1,10-phenanthroline iron(II) sulphate (4,7-dimethylferroin) | Pale blue | Red |
| Starch-KI | Blue | Colorless |
| Methylene blue | Blue | Colorless |
| Diphenylaminesulphonic acid | Red-violet | Colorless |
| Diphenylbenzidine | Violet | Colorless |
| Diphenylamine | Violet | Colorless |
| 3,3'-Dimethylnaphthidine | Purplish-red | Colorless |
| All leuco dyes | color | Colorless |

Acid-base reaction are colorless, but can be monitored with pH sensitive dyes. For example, bromophenol blue when exposed to a base such as sodium hydroxide turns blue. When blue-colored bromophenol blue is exposed to acids such as acetic acid it will undergo a series of color changes such as blue to green to green-yellow to yellow. Thus, acids and bases can be used as activators and corresponding pH dyes as indicators.

The following are representative examples of dyes that can be used for detection of bases: Acid Blue 92; Acid Red 1, Acid Red 88, Acid Red 151, Alizarin yellow R, Alizarin red %, Acid violet 7, Azure A, Brilliant yellow, Brilliant Green, Brilliant Blue G, Bromoscresol purple, Bromo thymol blue, Cresol Red, m-Cresol Purple, o-Cresolphthalein complexone, o-Cresolphthalein, Curcumin, Crystal Violet, 1,5-Diphenylcarbazide, Ethyl Red, Ethyl violet, Fast Black K-salt, Indigocarmine, Malachite green base, Malachite green hydrochloride, Malachite green oxalate, Methyl green, Methyl Violet (base), Methylthymol blue, Murexide, Naphtholphthalein, Neutral Red, Nile Blue, alpha-Naphthol-benzein, Pyrocatechol Violet, 4-Phenylazophenol, 1(2-Pyridyl-azo)-2-naphthol, 4(2-Pyridylazo) resorcinol Na salt, auinizarin, Quinalidine Red, Thymol Blue, Tetrabromophenol blue, Thionin and Xylenol Orange.

The following are representative examples of dyes that can be used for detection of acids: Acridine orange, Bromocresol green Na salt, Bromocresol purple Na salt, Bromophenol blue Na salt, Congo Red, Cresol Red, Chrysophenine, Chlorophenol Red, 2,6-dichloroindophenol Na salt, Eosin Bluish, Erythrosin B, Malachite green base, Malachite green hydrochloride, Methyl violet base, Murexide, Metanil yellow, Methyl Orange, Methyl violet base, Murexide, Metanil yellow, Methyl Orange, methyl Red Sodium salt, Naphtho-chrome green, Naphthol Green base, Phenol Red, 4-Phenylazo-aniline, Rose Bengal, Resazurin and 2,2'4,4',4"-Pentamethoxytriphenylmethanol.

Organic chemicals can be detected by the presence of their functional groups. Organic functional group tests are well known and have been developed for the detection of most organic functional groups, and can be used as the basis for the indicator-activator combination. For example, ceric nitrate undergoes a yellow to red color change when it reacts with an organic compound having aliphatic alcohol (—OH) as functional group.

Organic compounds having one or more of the following representative functional groups can be used in the device as activators: alcohols, aldehydes, allyl compounds, amides, amines, amino acids, anydrides, azo compounds, carbonyl compounds, carboxylic acids, esters, ethoxy, hydrazines, hydroxamic acids, imides, ketones, nitrates, nitro compounds, oximes, phenols, phenol esters, sulfinic acids, sulfonamides, sulfones, sulfonic acids, and thiols.

There are thousands of compounds under each functional group class listed above. For example, the following is a representative list of aminoacids that can be used as activators in the device: alanine, arginine, aspartic acid, cysteine, glutamic acid, glycine, histidine, hydroxylysine, lysine, methionine, phenylalanine, serine, tryptophan, tyrosine, alpha-aminoadipic acid, alpha, gamma-diaminobutyric acid, ornithine and sarcosine.

All alpha-amino acids undergo a colorless to purple-violet color when reacted with ninhydrin. In addition, the following are some specific amino acid tests: 1) Diazonium salts couple with aromatic rings of tyrosine and histidine residues to produce colored compounds. 2) Dimethylaminobenzaldehyde condenses with the indole ring of tryptophan under acid conditions to form colored products. 3) alpha-Naphthol and hypochlorite react with guanidine functions (arginine) to give red products.

The following is a representative list of alpha-amino acids that can be used as solid amines: Lysine, hydroxylysine, alpha, gamma- diaminobutyric acid and ornithine.

The following are some further selected examples of organic compounds that undergo a color change in the presence of a functional group test reagent:

Primary, secondary and tertiary aliphatic and aromatic amino bases can be detected with 2,4-dinitro chlorobenze. The observed color change is from colorless to yellow-brown.

Aliphatic amines, primary aromatic amines, secondary aromatic amines and amino acids react with furfural in glacial acetic acid to give violet Schiff bases.

A variety of triphenylmethane dyes react with sulfurous acid to produce a colorless leuco sulfonic acid derivative. When this derivative is allowed to react with an aliphatic or aromatic aldehyde, colored products are obtained.

Fuchsin, decolorized with sulfite when exposed to aliphatic and aromatic aldehydes, gives a violet blue color.

Malachite green, decolorized with sulfite when exposed to aliphatic and aromatic aldehydes, gives a green color.

Proteins and primary or secondary amines react with ninhydrin and many other stains to form colored products [Conn's Biological Stain, R. D. Lillie (Ed.), Williams and Wilkinson Company, 1977].

Guanidino Compounds react with a mixture of diacetyl and calcium oxide to give a red colored product.

A mixture of ferrous ammonium sulfate and potassium fluoride in dilute acid gives a yellow-orange to red-violet color when reacted with alpha-carboxylic acids of aromatic heterocyclic bases.

Ensols give a red color with neutral ferric chloride. Ensols give a green or blue copper derivative when reacted with copper II acetate.

A benzene solution of an acidic compound reacts with a mixture of Rhodamine B and 1% uranylacetate to give red or pink colored products.

A mixture of acidic compound, 2% iodide and 4% iodate when heated and exposed to starch or thyodene indicator gives a blue to violet color.

Organic oxidants which are active in neutral media can be detected by the yellow-brown color it produces with thio Michler's ketone (4-4'-bis-dimethylamino thio benzophenone). Organic oxidants react with a colorless tetrabase, i.e., tetramethyldiaminodiphenylmethane, to give a blue color.

A neutral or acidic solution of a reducing agent is reacted with aqueous phosphomolybdic acid and concentrated ammonic to give a blue-green color.

Test methods are also well known for the detection of inorganic compounds, their cations and anions, which are associated with a color change. These reactions and corresponding compounds can also be used in the device. Inorganic compounds and indicators for their detection are described in references: J. Bassett, R. C. Denney, G. H. Jeffery and J. Mendham, Vogel's Textbook of Quantitative Inorganic Analysis, Longman Scientific and Technical, p. 294, 1986.; Fritz Feigl, Vinzenz Anger and Ralph E. Oesper, Spot Test in Inorganic Analysis, Elsevier Publishing Company, 1972, p. 526–616.; Products for Analysis, Catalog of Hach Company, 1986–87. Representative examples of color changing reactions of inorganic cations and anions are listed below:

Cations: Aluminum ion reacts with alizarins to give a red precipitate; ammonium ion gives a red color with p-nitrobenzenediazonium chloride; copper ions react with cuproine to give a pink purple color; ferrous ion gives a red color with 2,2'-dipyridyl; ferric ion reacts with potassium ferrocyanide to give a blue color; magnesium ion gives a blue color with magneson; nickel ion reacts with dimethylglyoxime to give a red color; sodium ion gives a yellow color with zinc uranyl acetate; zinc ion reacts with dithizone to give a red color.

Anions: Acetate ion reacts with a mixture of lanthanum nitrate and iodine to give a blue color; bromide ion gives a red color with fluorescein; ferrocyanide reacts with ferric chloride to give a blue color; fluoride ion gives a pink color which turns yellow when reacted with a mixture of zirconium-alizarin; iodides react with nitroprusside to give a red color; thiocyanate ion reacts with ferric chloride to give a red color.

The synthesis of dyes generally involves the reaction between two or more colorless intermediates to produce a colored product (references R.L.M. Allen, Color Chemistry, Appleton-Century, Crofts, 1971; K. Venkatraman, The Chemistry of Synthetic Dyes, Vol. II, Academic Press, New York, 1952). Often, mild reaction conditions are used. Some typical examples of dye syntheses are as follows: (1) Indrophenol Blue: The reaction of alphanaphthol with p-nitroso-dimethylaniline in the presence of acid gives indophernol blue. (2) Yellow Couplers: Benzoylacetanilides react with N,N'dialkyl-p-phenylenediamine in the presence of silver ions to afford yellow azamethine dye. (3) Azo Dyes: Benzoisooxazolones give yellow azo dyes when reacted with N,N'-dialkyl-p-phenylenediamine. (4) Magenta Dyes: Pyrazolone couplers react with N,N' dialkyl p-phenylenediamine in the presence of silver bromide to give magenta azamethine dye. (5) Pyronine Group: The condensation of two moles of m-dialkylamino phenol with an anhydride of a dicarboxylic acid in the presence of a mineral acid gives the Pyronine group of dyes viz. Rhodamine S. (6) Triphenylmethane derivative: Reaction of o-chlorobenzaldehyde with 2-methyamino-p-cresol gives a brilliant red dye, Rhodamine 5G. (7) Pigments: Condensation of 4,5,6,7 tetrachloroiso-indolin-1-one with aromatic amines give rise to pigments called Irgazine. These pigments vary in color from yellow, orange, red and brown depending on the aromatic amine.

Several rearrangement reactions are known in organic chemistry (Advanced Organic Chemistry, Third Edition, Jerry, March, p. 942-1047). Some of these rearrangements are: Pinacol Rearrangement, Dienone-Phenol Rearrangement, Wallach Rearrangement, Fischer-Indole Synthesis, Favoroski Type Rearrangements, Curtius Rearrangement, Lossen Rearrangement. Some of the compounds involved in these rearrangement reactions can be used for preparation of the device. An example of a rearrangement reaction is the pinacol rearrangement where 1,2 vic-diols, when reacted with a mineral acid, rearrange to form either an aldehyde or ketone which in turn can be detected with 2,4- dinitrophenylhydrazine.

Some of the above mentioned rearrangement reactions are also known as Organic Name Reactions. There are several other organic name reactions known (The Merck Index, Tenth Edition, pp. ONR-1 to ONR-100). Some of these name reactions are: Bayer-Drewson Indigo Synthesis, Baudisch Reaction, Meisenheimer Complexes, Rosenheim Color Test, Zimmerman Reaction. An example of a reaction involving two reactants A and B to produce a colored product C is the Baudisch Reaction where O-nitrosophenol reacts with a copper salt, to give a colored product.

A large number of adsorption indicators are known (Indicators, Edmund Bishop, Pergaman Press 1972, Ch 7 p. 437-468). some of these indicators along with the ions responsible for the color change can be used in the device. Table 2 below lists some ions, indicators and associated color changes (ppt. indicates precipitate):

TABLE 2

A representative list of ions useful as activators and corresponding indicators and color changes.

| Ions | Indicator | Color Change |
| --- | --- | --- |
| Ag+ with Br− | Rhodamine 6G | pink → violet |
| Ag+ Br− | Phenosafranine | Blue → Red. |
| Cl−Br−,I− | Fluorescein | Yellow green → Pink |
| Cl−,Br−Ag+ | Phenosafranine | Red → Blue |
| I− Ag+ | Erythrosin | Yellowish → Reddish Red → Violet |
| Scn− Ag+ | Alizarin Red | Yellow → Red |
| | Aurazine | Green → Orange Red Fluor. → Fluor. |
| Scn− (Ag+) | Dichloro(R)-Fluoresin | Yellow green → Red |
| | Eosin | Pink → Red-Violet |
| | Rose Bengal | Red → Purple |
| | Tartrazine | Colorless → Green |
| Zn[Fe(CN)$_6$)$_4$$^-$] | Methyl Red | Pink → Yellow |
| Hg$_2$$^{2+}$ (cl + Br) | Diphenylcarbazide | Bluish → Colorless |

A large number of reactions are assembled with a change in fluorescence rather than a color change in the visible region. Such compounds can be used as indicator/activator pairs in the device. The time-temperature history and thus shelf life can be monitored by monitoring the change in fluorescence. Several fluorescent indicators are known (Vogel's Textbook of Quantitative Inorganic Analysis, Fourth Edition, Longman, p. 776.) and some of these along with their respective color change are listed in Table 3 below:

TABLE 3

A representative list of fluorescent dyes and their color changes

| Indicator | Color Change |
| --- | --- |
| Acridine | Green-to-violet blue |
| 2-Hydroxycinnamic acid | Colorless-to-green |
| 3,6-Dihydroxyphthalimide | Colorless-to-Yellowish Green |
| Eosin | Colorless-to-green |
| Erythrosin B | Colorless-to-green |
| Fluorescein | Colorless-to-green |
| 4-Methyl-Aesculetin | Colorless-to-blue |
| 2-Naphthoquinoline | Blue-to-colorless |
| Quinine sulfate | Blue-to-violet |
| Quininic Acid | Yellow-to-blue |

The device and its modifications are not limited to activator—indicator combinations which are associated with chemical reactions for producing the color change. Also included are any two or more compounds which can undergo a noticeable or measurable physical change, which can be monitored by appropriate analytical equipment. Such changes include particle size, transparency, electric conductivity, magnetism and dissolution. For example, a change in conductivity can be monitored by an electrometer.

A large number of organic and inorganic compounds undergo decomposition with time and temperature which can be utilized in the instant device. Either the starting material or the decomposition products can be monitored. For example, ammonium bicarbonate decomposes with time and temperature to produce ammonia as one of the decomposition products which can be monitored with a pH dye. Some typical example of organic and inorganic compounds which undergo thermal decompositions include sodium carbonate, sodium bicarbonate, blowing or foaming agents such as azodicarbonamide, peroxides as benzoyl peroxide, and nitroureas. The devices made from these compounds can also be activated by temperature, i.e. by heating the completely assembled device above the decomposition temperature of the compound. As long as the parent compounds do not migrate and the decomposed product(s) can be detected with an indicator which would be incorporated in the indicator matrix, they can be used in the invention device.

The method of activation of the invention device is not limited to pressure lamination. The device can also be activated by temperature as described above. If the proper activator is used the device can be activated by radiation as well. If the activator is microencapsulated, it can be released by applying pressure or temperature. If the activator can be decomposed by radiation, the assembled device can be activated by radiation (see "Effect of Radiation on Materials and Components" by J. Kircher and R. Bowman (Ed.). Reinhold Publishing Corp., N.Y. and "Radiation Effects in Materials". Vol. 2, A. Charlesby (Ed.) Pergamon Press, N.Y.). For example, diphenyliodonium chloride produces HCl when irradiated with UV light. Similarly triphenylsulfonium hexafluoroantimonate produces superacids such as HF and HAsF$_6$. These acids are the activating agents that can diffuse to contact a pH dye.

Photoresist compounds (see, Encycl. Polym. Sci. Eng. Vol 9, 97 (1987) and Amer. Chem. Soc. Symp. Se. s No. 219 (1983) undergo degradation to provide lo molecular weight materials upon irradiation with high energy radiation such as UV, x-ray, gamma ray and electrons, can also be used as activators. Positive photoresists which can be utilized in such manner include polydimethylketone, halogenated polyethylene, polymethylmethacrylate, poly(olefin sulfone) and poly(hexafluorobutyl) methacrylate. Any compound which does not migrate from the activator matrix and undergoes chemical reaction with radiation to produce compound(s) which can migrate through the activator matrix and can be detected by an indicator in the indicator matrix can be used as the activator in this device.

Certain compounds, especially conjugated polymeric compounds, when reacted with certain oxidizing, reducing agents or complexing agents undergo a change in electrical and magnetic properties. The electrical conductivity can be electronic or ionic. For example, when polyacetylene is exposed to iodine vapor the conductivity of polyacetylene increases from $10^{-8}$ to $10^3$ S/cm. TTF (tetrathiafulvalene) when reacted with TCNQ (tetracyanoquinodimethane), undergoes several orders increase in conductivity. Similarly, when conductive polyacetylene is exposed to ammonia the conductivity decreases back to $10^{-8}$.

Certain compounds when in a reactive state undergo a change in transparency, becoming opaque or more transparent. See for example, U.S. Pat. Nos. 4,345,470 and 4,397,570 both to C. Hot et. al. and assigned to Pymah Corp.. Fine powder of most solid compounds are opaque. When such opaque compounds are dissolved, they become clear or transparent. Also as an illustration, opaque benzoic acid in crystalline form can be layered in the indicator matrix positioned on top of a display message, such that the display message is hidden. Triacetin, for example, which can dissolve benzoic acid, can be utilized in the activator layer as the activator and can migrate through the composite matrix layer to contact the benzoic acid to dissolve it and thus reveal the underlying message.

Certain compounds undergo an observable color change only by a physical reaction. For example, a number of dyes, when dissolved, undergo a color change. Some of the partially polymerized diacetylenes undergo a blue to red color change when exposed to a solvent or its vapor. Such reactions and activator/indicator systems can also be used in the device.

In principle, there is no limit in the selection of indicators and activators for use in the devices. Any two or more compounds which can undergo a noticeable or measurable physical or chemical change can be used in the device. The selection of the activators and indicators for the actual device for a particular perishable will depend on factors including the toxicity and hazardous nature of the chemicals/reactions.

Preferred materials for indicators and activators are those which are not affected by ambient conditions such as light, air, air pollutants, and moisture and are nontoxic. Water insoluble food additive/ingredients are particularly preferred as activators. Colors and dyes/pigments approved for dyeing and printing and food colors are preferred indicators.

The following discussion relates to a description of the shelf life of a perishable product, the Arrhenius characteristics of the product decay process, and methods for altering the invention device to match the activation energy and rate constant of color change with the activation energy and rate constant of product decay of the perishable in the temperature range of monitoring.

All perishable foods have a measurable shelf-life. Consumer acceptability of any product is mainly judged by its aesthetic appearance at the time of sale. The other aspects of quality, such as nutritional, microbiological and toxicological values are of prime importance, but the consumer is not qualified to make any judgements regarding them.

The main environmental factor that results in increased loss of quality and nutrition for most perishables is exposure to increased temperature. The higher the temperature the greater is the loss of the quality. Hence it is extremely important to be able to monitor the shelf life of foods.

The shelf life of most common foods has been reviewed by Labuza [T. P. Labuza, "Application of Chemical Kinetics to Deterioration of Foods", J. Chem. Educ., Vol. 61, page 348 (1984), and T. P. Labuza "Shelf-life Dating of Foods", Food and Nutrition Press, Westport, Conn. (1982)]. The shelf life of a large number of foods and beverages has also been reported in a recent book edited by Charalambous, see "The Shelf-Life of Foods and Beverages", by G. Charalambous (Ed.), Elsevier, New York, 1988.

As previously described above in the discussion of FIG. 1, a plot of the logarithm of the reaction rate as a function of the reciprocal of (absolute) temperature (1/T) gives a straight line. The slope of each line is equal to the activation energy divided by the gas constant, "R". A comparatively steeper slope means the reaction is more temperature dependent; i.e. as the temperature increases, the reaction increases at a faster rate. Also, a lower value for the Y intercept, i.e. value for ln k, indicates a faster induction time for either color change or product decay.

It is clear from the above discussion that the activation energy and shelf life of the perishable should match with those of the time-temperature indicator, in the temperature region to be monitored to compensate for temperature variations during storage. In an ideal case, the kinetic-plot of the indicator should overlap the kinetic-plot of the perishable it is applied to.

Figure 2:
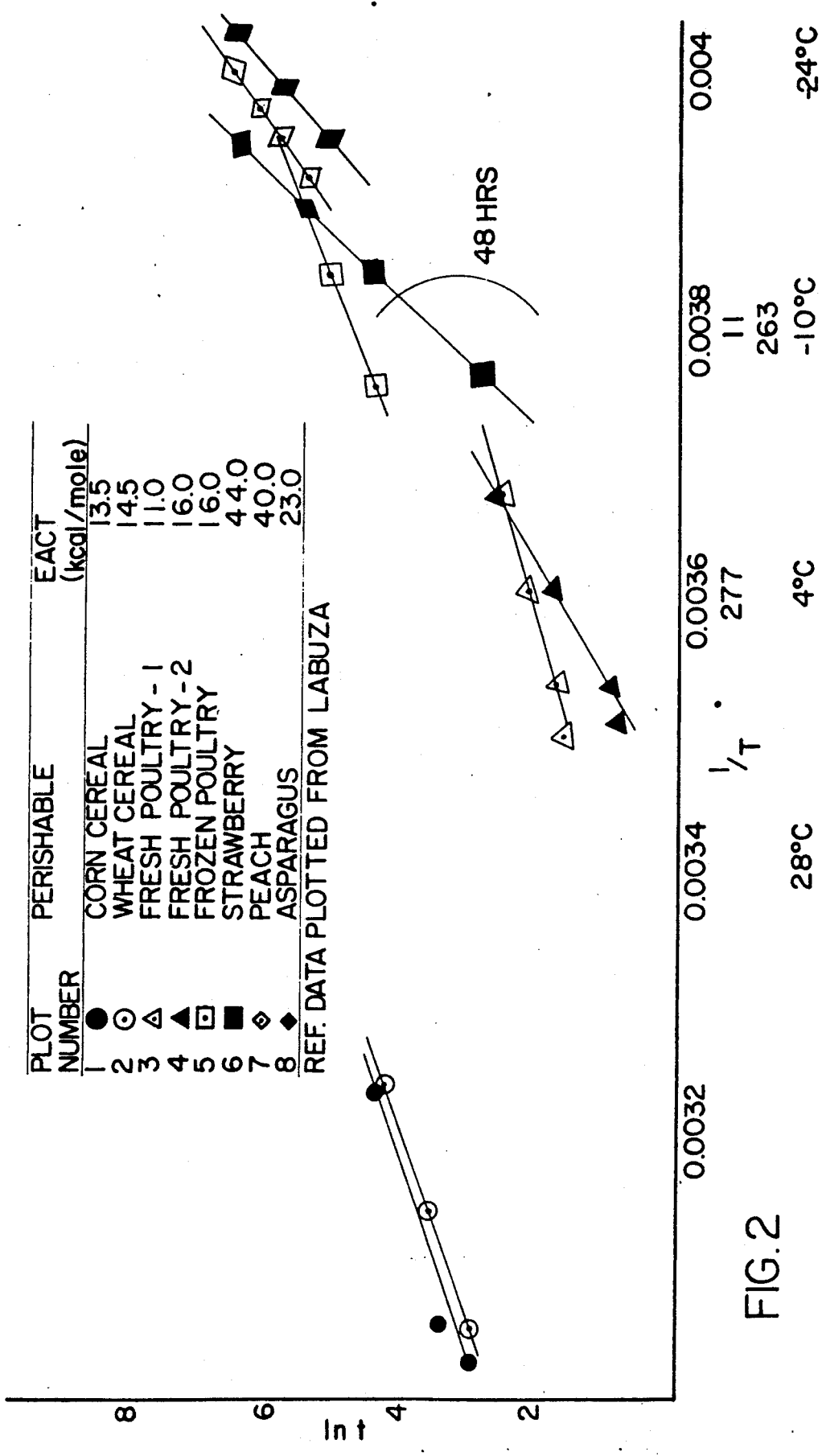
FIG. 2 illustrates kinetics diagrams for various common perishable foods illustrating relative stabilities, i.e. shelf-lives, at different temperatures.

FIG. 2 shows Arrhenius plots for some selected perishables. It can be readily seen that different foods have different activation energies and shelf lives as a function of the particular mode of product decay. The activation energy for most, simple hydrolysis reactions is 10-20 kcal/mole, lipid oxidation is 15-25 kcal/mole, nonenzymatic browning 20-40 kcal/mole and, enzyme and microbial destruction is usually higher than 40 kcal/mole. For example, the activation energy of deterioration of beef can vary from 8 to 100 Kcal/mole (see Labuza, supra). The data summarized by Labuza indicate that perishable foods can have shelf life of a few hours to a few years and the associated activation energy can vary from 5 to 100 Kcal/mole. Some perishables have the same activation energy of decay but different shelf lives and vice versa. For most perishables the activation energy and the shelf life range from 10 to 70 kcal/mole and 6 hours to 5 years respectively. There are thousands of perishables, each having essentially different kinetics and modes of deterioration. Thus the time-temperature indicators for recording their thermal degradation must be extremely flexible to match the shelf lives and the activation energies of the perishables.

As stated above, in the case of an ideal shelf-life indicator, the plot of the logarithm of time required for color change versus 1/T (Arrhenius plot) of the device should essentially overlap the plot of the logarithm of the shelf-life versus 1/T (Arrhenius plot) of the perishable. In such case, the device will change color when the shelf-life of the perishable expires irrespective of fluctuations in the storage temperature. In order to overlap the Arrhenius plot of the device with that of the perishable, the slope of the Arrhenius plot of the device is shifted as shown in schematically in FIGS. 6a and 6b. By changing the slope and shifting the Arrhenius plot of the device, one can overlap the Arrhenius plot of any perishable with that of the device.

For a given temperature, the time required for the color change, and the activation energy, can be varied by varying the parameters given in Table 4.

Table 4

Major Classes of Parameters for Varying the Time Required for the Color Change and the Activation Energy of the Tape Device 1. Thickness of the matrices
2. Concentration of the activator
3. Concentration of the indicator
4. Concentration of other additives in the matrices
5. Nature of the activator matrix
6. Nature of the indicator matrix
7. Nature of the barrier matrix
8. Nature of the activator
9. Nature of the indicator
10. Nature of additives in the matrices
11. Nature of the interface between two matrices
12. Mixture of different matrices
13. Mixture of different activators
14. Mixture of additives in the matrices
16. Degree of formation of solid solution between matrix and activator/additive The thickness of the indicator, activator and barrier matrices can be as desired and will for practical purposes be, independently, in the range of about 0.001 to 5 mm. Preferably, for food storage monitoring of perishables, the thickness of each matrix layer is independently in the range of 0.05 to 0.5 mm. Also, preferably the matrices are of approximately equal thicknesses. Generally, varying the thickness of a matrix will alter the rate at a particular temperature on the Arrhenius plot of a given device. Larger thicknesses will decrease the given rate of color change production.

The thickness of the barrier matrix can be anywhere from 0.001 to 5 mm. or larger. Preferably, the thickness of the barrier layer in relation to the indicator and activator layers is about 0.005 to 1 mm.

The concentration of activator in solid solution in the activator matrix is in the region of 0.001 to 0.9 g./cc of matrix and preferably 0.15 to 0.5 g./cc. of matrix.

The indicator can either be deposited as a layer on the indicator film 1, in a thickness of 0.01 to 5 mm., or can also as the activator, be in solid solution in the indicator matrix, and if so, is present in approximately the same concentration range as Other additives which can be utilized in the matrices include those materials which, unless and until desired do not react with the matrices, activators, indicators or film. It should preferably, form a solid solution at least, with the activator matrix. It can be an inert compound which just dilutes the concentration of activator or indicator. It can also aid in forming the solid solution of the activator.

The additive can also be a reactive compound. For example, if the activator is an acid, e.g. benzoic acid, a basic compound such as dodecylamine, can be added as an additive in the indicator matrix to chemically control and introduce the induction period. The acid will react first with the amine until all the amine is reacted, and then react with the dye to introduce the color change.

The additive can also be a compound which complexes or interacts with the activator to slow down, or accelerate its diffusion.

The concentration of the additive in the individual matrix layers can range from 0.001 to 0.5 g/cc The nature of the activator, indicator and barrier matrices can be varied by using independently the polymer films described hereinabove, also including pressure sensitive adhesives.

Adhesives, for example, include the use of synthetic elastomers, acrylates, silicone, synthetic latex and vinyl acetate, as representative examples. The activation energy will in general, for a particular indicator-activator system, increase from about 10–70 kcal/mole proceeding down the above-given matrix series. In general, varying the thickness of a matrix will alter the induction period, i.e. the time required for color change, while varying the nature of the matrix will alter the Eact.

Changing the nature of the indicator or activator in a given device will generally alter the Eact of the device as well as the time required for color change. Changing only the concentration of the indicator or activator will generally only affect the induction period for color change. The larger the concentration, in general, the faster the rate and lesser time for color change production.

Also, changes in the crystallinity or amorphous nature of the matrix can affect the Eact. Generally, the more amorphous or less crystalline the matrix, the lower the Eact.

Also, changes in the polarity of the matrix and activator can effect the Eact. As a general rule, if the polarity of the activator and the matrix through which it is migrating are substantially the same, then the Eact will be higher. The larger the differences between the respective polarities, the lower the Eact in general. For example, see EXAMPLES 2 and 3, and examples 13 and 14.

The polarity of the interface between the two matrices affects the Eact following the above rule as in EXAMPLE 3.

The polarity rule as applied to mixtures of different matrices also affects the Eact as seen in EXAMPLE 4.

The use of mixtures of different additives also affects the Eact by the polarity rule as seen in EXAMPLE 6; as well as the interaction between the matrix and activator/additive combination as seen in EXAMPLES 2 to 6.

The degree of formation of solid solution between the matrix and activator/additive affects the Eact by the general rule that the greater the degree of solid solution the lower the Eact for the system. This is seen in EXAMPLE 10.

Although the time required for the color change can be varied by all of the factors listed in Table 4, the activation energy of color change can be mainly varied by factors 5 through 16 and their combinations.

As described above, the activation energy of the device, can be readily varied to match that of the perishable. These various methods of altering the activation energy will become more readily apparent in the examples where the methods are illustrated for simplicity by the two-layer and three-layer uniform thickness devices.

The color changing tape device of the instant invention has the following combination of major characteristics, benefits and advantages over those available commercially and those reported in the literature.
1. It can be fashioned into a small and simple device by conventional technology.
2. The device is essentially solid state and water-impermeable.
3. The device can be made inactive until applied to the perishable container.
4. The unactivated device can be made to have an extremely long shelf-life.
5. The device can withstand normal mechanical abuses.
6. Proper activator/indicator combinations are unaffected by humidity and other adverse ambient conditions.
7. The activator/indicator combinations can be selected from a wide variety of nonhazardous chemicals, including food additives and food ingredients.
8. The color change is irreversible.
9. The time required for the color change can be varied by several orders of magnitude.
10. The activation energy can be varied from 3 to 70 kcal/mole.
11. The degradation kinetics of perishables can be matched with the kinetics of color change of the device.
12. The device can be used for recording and monitoring the thermal degradation of most perishables.
13. The consumer can read the residual shelf-life from the color of the device.
14. The device can be designed to be read by conventional electro-optical equipment.

The following examples are illustrative of carrying out the claimed invention but should not be construed as being limitations on the scope or spirit of the instant invention.

EXAMPLES

IA. Materials Used in the Invention

ADHESIVES

The adhesives used in the present invention are listed below in table 5.

TABLE 5

List of adhesives used as a matrix and their compositions.

| Chemical Name of Adhesive | Percentage of solid | Manufacturer & Product # | Solvent medium | Thickness (mil)[a] |
|---|---|---|---|---|
| Synthetic Elastomer | 25 | 3M Scotch grip 4910 NF | 1,1,1-Trichloro-ethane | 1.5 |
| Synthetic Elastomer | 25 | 3M Scotch grip 4914 | Oxy-hydrocarbon | 1.5 |
| Acrylate | 42 | National Starch Duro Tack, 80-1068 | Ethyl acetate, Heptanes, Toluene | 1.5 |
| Acrylate | 44 | 3M Scotch grip 4268 | Water emulsion | 3.0 |
| Acrylate | 45 | Testworth Lab. Paralac DF-C119 | Oxy-hydrocarbon | 2.0 |
| Silicone | 55 | General Electric PSA529 | Toluene | 3.0 |
| Synthetic Latex | 50 | United Resin Corp. 40-0033 | Xylene | 3.0 |
| Vinyl Acetate | 60 | United Resin Corp. J8905 | Water emulsion | 3.0 |

[a]Thickness of the adhesive layer in the device.

IB. ACTIVATOR/INDICATOR PAIRS

The following table is a representative list of activator/indicator combinations useful in the present invention:

TABLE 6

List of activator/indicator pairs used in the present invention

| Type of Reaction | Indicator @ | Activator | Color change | Comments |
|---|---|---|---|---|
| Dissolution | pp4BCMU | Triacetin | Blue-red | Unaffected by moisture. |
|  | " | Tributaryn | " |  |
|  | " | Linoleic acid | " |  |
|  | " | Heptanoic acid | " |  |
| pH Change | BPB-Na salt | Adipic acid | Blue-green-yellow | Food additives |
|  | " | Benzoic acid | " |  |
|  | " | Citric acid | " |  |
|  | " | Vitamin-C | " |  |
|  | PTM | Citric acid | Colorless-red |  |
|  | " | Vitamin-C | " |  |
| Oxidation | LeucoMG | Ammoniumper sulfate | Colorless-green |  |
| Reduction | MG | Sodiumsulfite | Green-Colorless |  |
| Decomposition | BPB | Sodiumcarbonate | Yellow-green-blue |  |
|  | " | Sodiumbicarbonate | " |  |

Notes @:
pp4BCMU = Partially polymerized 4BCMU
BPB-Na salt = Bromophenolblue sodium salt
BPB = Bromophenolblue (water insoluble)
PTM = pentamethoxytriphenylmethane
LeucoMG = Leucomalachite green
MG = Malachite green

METHODS

The following methods were used for preparation of tapes and devices:

Method 1. General Method of Preparinq Solutions of Indicators and Activators in a Pressure Sensitive Adhesive Matrix A known weight, e.g. 0.2 g of an indicator or 1.0 g of an activator, a known weight (e.g. 5 g) of a solvent, (if used for the indicator, and required for the activator to be dissolved) and a known weight (e.g. 4 g) of a pressure sensitive adhesive matrix (see above table 5) were placed in a 25 ml polypropylene tube and dissolved by spinning the mixture in a Rotavapor Model-R110 (Brinkman Instrument Inc., Westbury, N.Y.) for 5 minutes. The resulting solid solution was used for coating.

Method 2. General Method of Preparing Solutions of Indicators and Activators in an Ink Medium (Layers)

A known weight, e.g. 0.1 g of an indicator or 1.0 g of an activator, a known weight (e.g. 9.0 g) of about 4% solution of ink matrix (e.g. cellulose nitrate) in a suitable solvent (e.g. ethylacetate) were placed in a 25 ml polypropylene tube and dissolved by spinning the mixture in a Rotavapor Model-R110 (Brinkman Instrument Inc., Westbury, N.Y.) for 5 minutes. The resulting solution was used for coating.

Method 3. General Method of Coating for Adhesive Medium

A 5 mil thick, 8×18 inch polyester sheet (Mylar, DuPont) was laid flat on a x-y recorder (disconnected from a Electron Spin Resonance Spectrophotometer, Model E-4, Varian, Palo Alto, Calif.) and held in place by an inbuilt suction of the recorder. A Bird type wet film applicator of cut depth 0.0015 or 0.006 inch (obtained from Paul Gardner Company, Inc., Pompano Beach, Fla.) was placed at one end of the polyester sheet against the arm of the recorder. 10 g of the indicator or activator mixture prepared according to the procedure described in Methods 1 or 2 was poured in a straight line in front of the wet film applicator and the applicator was moved across the face of the film at a constant speed of 4" per minute by setting the scanning speed of the recorder. The resulting film was allowed to dry for about 24 hours at room temperature. This constitutes the indicator or activator tape.

Method 4. General Method for Device Activation

The device was activated (assembled) by laminating the indicator tape and activator tape so that the activator matrix faces the indicator matrix. At least one of the matrices is a pressure sensitive adhesive. Gentle pressure using a hand roller or finger pressure was applied to obtain uniform bonding between the indicator and activator media.

Method 5. General Method of Preparation of Stationary 4BCMU Indicator tape

A known weight (e.g. 1 g) of 4BCMU [a diacetylene, R—C≡C—≡C—R, where R is $(CH_2)_4OCONHCH_2COO(CH_2)_3CH_3$] synthesized according to procedure of Patel (Polymer Preprint, 19(2), pp 154–159, (1978) and U.S. Pat. No. 4,452,995 assigned to Allied Chemical Corp.), 5 g of chloroform and 4 g of a polymeric resin (e.g. an adhesive or ink matrix) were placed in a plastic tube and dissolved by spinning the mixture in a Rotavapor for 5 minutes according to procedure describe in Method 1.

The indicator tape was prepared by coating the above solution according to the procedure described in Method 3. The tape was allowed to dry for a day. The coating of 4BCMU was then exposed to a short wavelength (254 nm) UV lamp for partial polymerization of 4BCMU, until the colorless coating turned moderately blue. This partially polymerized 4BCMU is referred to hereinafter as "pp4BCMU".

Many partially polymerized diacetylenes including 4BCMU undergo a blue to red color change when contacted with a solvent which dissolves the unreacted monomer. 4BCMU was experimentally tested to determine whether an indicator/activator system which undergoes a physical reaction can be used for preparation of the device.

Method 6. General Method of Preparation of Activator Tape for 4BCMU

A known weight (e.g. 1 g) of an activator (e.g. triacetin) which has ability to dissolve 4BCMU monomer and 9 g of polymeric medium (e.g. a pressure sensitive adhesive matrix layer) were mixed according to the general procedure describe in Method 1.

The activator tape was prepared by coating the above solution according to the procedure described in Method 3. The tape was allowed to dry at least for a day.

The stationary device utilized for Examples 2 to 8 was a two-layer device, in which the activator tape was made by Method 6, the indicator tape by Method 5, and the two layers laminated together according to Method 4.

The effects of various parameters on time required for the color change and the activation energy of the device were experimentally studied. Because of the voluminous data, tables of time required for the color change at different temperatures are not presented. Instead, the same data are presented in form of plots of logarithm of time required for the color change versus reciprocal of temperature, the Arrhenius plots. The activation energy was calculated from slopes of the Arrhenius plots. The plots are illustrated as FIGS. 7–12.

EXAMPLE 1

Control Devices

The indicator, pp4BCMU was incorporated into a adhesive listed in table 5. Corresponding activator tapes were prepared from the same adhesives without using any kind of activators. Both the tapes were thoroughly dried. The devices were activated with applying the activator tapes over the indicator tapes according to method 4. None of the device change color after some months at room temperature indicating that the color change in the examples 2–8 is due to the activators used.

EXAMPLE 2

Effect of the Nature of the Matrix on the Activation Energy When the Activator and Indicator Matrices are the Same Material The indicator, pp4BCMU and the activator, triacetin were incorporated into the same matrix materials. Three different matrix materials were used. The Arrhenius plots for these systems are shown in FIG. 7. The effect of variation of matrix on the activation energy when the indicator and the activator are in the same matrix material are presented in the table below. As can be seen from table 7, the activation energy can be varied from 31 to 62 kcal/mole by changing the nature of the matrix material.

TABLE 7

Variation in activation energy when indicator and activator matrices are the same materials. Concentrations of activators and indicators in the matrix are given in the parentheses.
SYSTEM:
Indicator Tape: Indicator: pp4BCMU, Concn.: Varied; Matrix: Varied
Activator Tape: Activator: TA; Concn.: Varied; Matrix: Varied

| Indicator System | | Activator System | | Activation Energy (kcal/mole) | Plot # FIG. 7 |
|---|---|---|---|---|---|
| Indicator | Matrix | Activator | Matrix | | |
| pp4BCMU (17%) | Silicone | TA (17%) | Silicone | 62 | 1 |
| pp4BCMU (30%) | Acrylate/TW | TA (22%) | Acrylate/TW | 34 | 2 |
| pp4BCMU (8%) | Elastomer | TA (31%) | Elastomer | 31 | 3 |

Notes:
See table 5 for the manufacturers of the adhesives an their properties. Unless specified concentration of catalyst for the silicone resin was 3%.
TA = Triacetin, TW = Testworth Lab. and pp4BCMU = Partially polymerized 4BCMU

EXAMPLE 3

Effect of the Nature of the Matrix on the Activation Energy When Activator and Indicator Matrices are Different The indicator, pp4BCMU was incorporated into a synthetic elastomer and the activator, triacetin was incorporated in several other matrices. The Arrhenius plots for these systems are shown in FIG. 8. The effect of variation of matrix on the activation energy when the indicator and the activator are in different matrices are presented in table 8. As can be seen, the activation energy can be varied from 20 to 50 kcal/mole.

TABLE 8

Variation in the activation energy when indicator and activator matrices are different materials. Concentrations of activators and indicators in a particular matrix are given in the parentheses.
SYSTEM:
Indicator Tape: Indicator: pp4BCMU, Concn.: 8%; Matrix: Elastomer
Activator Tape: Activator: TA, Concn.: Varied; Matrix: Varied

| Indicator System | | Activator System | | Activation Energy (kcal/mole) | Plot # in FIG. 8 |
|---|---|---|---|---|---|
| Indicator | Matrix | Activator | Matrix | | |
| pp4BCMU (8%) | Elastomer | TA (31%) | Elastomer | 31 | 1 |
| pp4BCMU (8%) | Elastomer | TA (22%) | Acrylate/TW | 50 | 2 |
| pp4BCMU (8%) | Elastomer | TA (22%) | Acrylate/NS | 45 | 3 |
| pp4BCMU (8%) | Elastomer | TA (22%) | Silicone (0.6% Catalyst) | 44 | 4 |
| pp4BCMU (8%) | Elastomer | TA (22%) | Vinylacetate | 39 | NOT SHOWN |
| pp4BCMU (8%) | Elastomer | TA (22%) | Silicone (3% catalyst) | 20 | " |

Notes:
See table 5 for the manufacturers of the adhesives and their properties. Unless specified concentration of catalyst for the silicone resin was 3%.
TA = Triacetin, TW = Testworth Lab., NS = National Starch, and pp4BCMU = Partially polymerized 4BCMU

EXAMPLE 4

Effect of Matrix Mixtures on the Activation Energy

Figure 9:
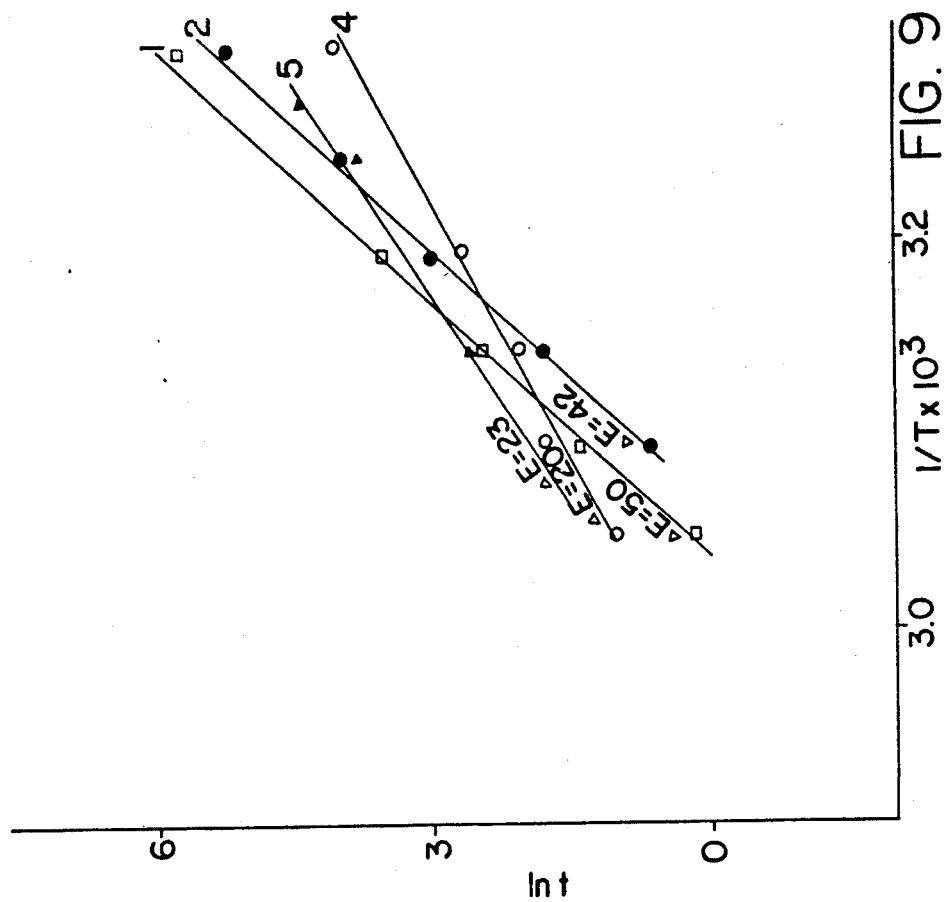

The indicator, pp4BCMU was incorporated in a synthetic elastomer and the activator, triacetin was incorporated into mixtures of four different matrix materials. The Arrhenius plots for these systems are shown in FIG. 9. The effect of matrix 0 mixtures on the activation energy is presented in table 9. It can be seen that the activation energy can be varied from 20 to 50 kcal/mole by selecting and mixing appropriate amounts of the matrix mixtures for the activator.

TABLE 9

Effect of matrix mixtures on the activation energy. Concentrations of activators and indicators in the matrix materials are given in the parentheses.
SYSTEM:
Indicator Tape: Indicator: pp4BCMU, Concn.: 8%; Matrix: Elastomer
Activator Tape: Activator: TA, Concn.: Varied; Matrix: Varied

| Indicator System | | Activator System | | Activation Energy (kcal/mole) | Plot # in FIG. 9 |
|---|---|---|---|---|---|
| Indicator | Matrix | Activator | Matrix | | |
| pp4BCMU (8%) | Elastomer | TA (22%) | Acrylate/TW | 50 | 1 |
| pp4BCMU (8%) | Elastomer | TA (22%) | Elastomer + Acrylate/TW (7:3) | 42 | 2 |
| pp4BCMU (8%) | Elastomer | TA (22%) | Elastomer + Acrylate/TW (3:7) | 40 | NOT SHOWN |
| pp4BCMU (8%) | Elastomer | TA (22%) | Silicone (3% catalyst) | 20 | 4 |
| pp4BCMU (8%) | Elastomer | TA (22%) | Silicone + Elastomer (:) | 23 | 5 |

TABLE 9-continued

| | | | | | |
|---|---|---|---|---|---|
| pp4BCMU (8%) | Elastomer | TA (31%) | Elastomer | 31 | NOT SHOWN |

Notes:
See table 5 for the manufacturers of the adhesives and their properties. Unless specified concentration of catalyst for the silicone resin was 3%.
TA = Triacetin, TW = Testworth Lab., and pp4BCMU = Partially polymerized 4BCMU

EXAMPLE 5

Effect of Different Activators on the Activation Energy

Figure 10:
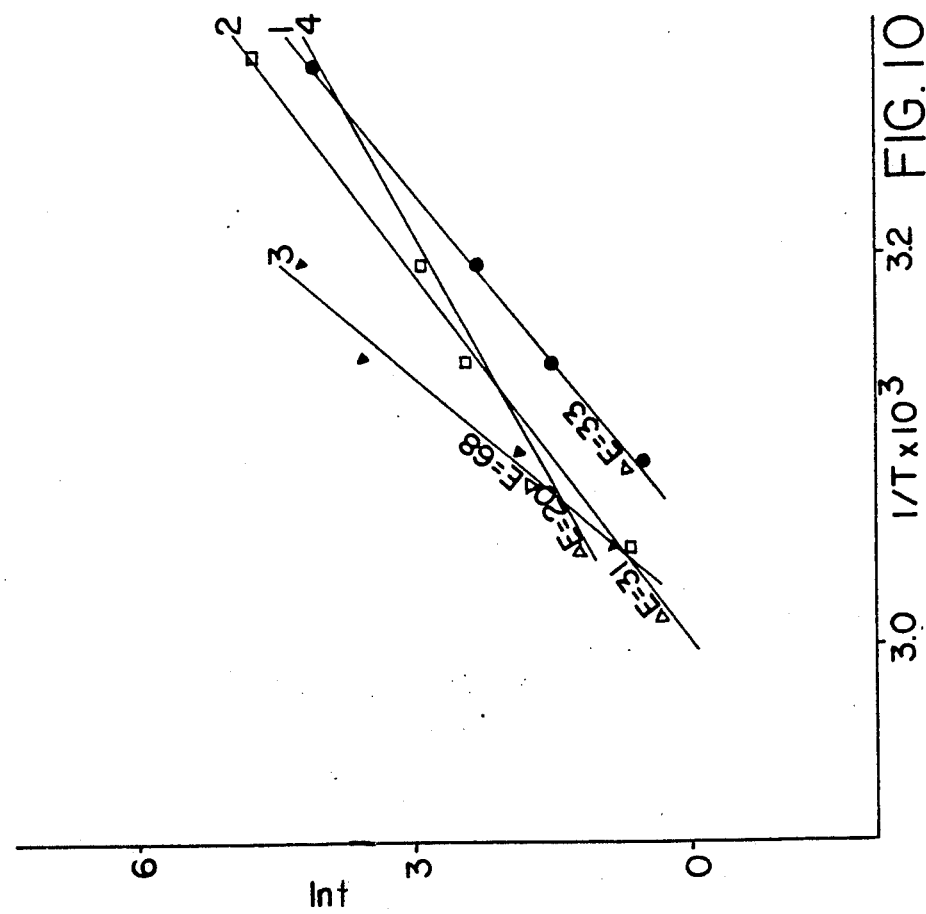

The indicator, pp4BCMU was incorporated into a synthetic elastomer and different activators, including triacetin and linoleic acid were incorporated into silicone and elastomer matrices. The Arrhenius plots for these systems are shown in FIG. 10. The effect of different activators on the activation energy is presented in table 10. It is seen that the activation energy can be varied from 68 to 20 kcal/mole by selecting a proper activator.

TABLE 10

Effect of variation of activator on the activation energy. Concentrations of activators and indicators in the matrix are given in the parentheses.
SYSTEM:
Indicator Tape: Indicator: pp4BCMU, Concn.: 8%; Matrix: Elastomer
Activator Tape: Activator: Varied, Concn.: Varied; Matrix: Varied

| Indicator System | | Activator System | | Activation Energy | Plot # in |
|---|---|---|---|---|---|
| Indicator | Matrix | Activator | Matrix | (kcal/mole) | FIG. 10 |
| pp4BCMU (8%) | Elastomer | LA (28%) | Elastomer | 33 | 1 |
| pp4BCMU (8%) | Elastomer | TA (31%) | Elastomer | 31 | 2 |
| pp4BCMU (8%) | Elastomer | LA (28%) | Silicone | 68 | 3 |
| pp4BCMU (8%) | Elastomer | TA (22%) | Silicone | 20 | 4 |

Notes:
See table 5 for the manufacturers of the adhesives and their properties. Unless specified concentration of catalyst for the silicone resin was 3%.
TA = Triacetin, LA = Linoleic acid, and pp4BCMU = Partially polymerized 4BCMU

EXAMPLE 6

Effect of Activator Mixtures on the Activation Energy

Figure 11:
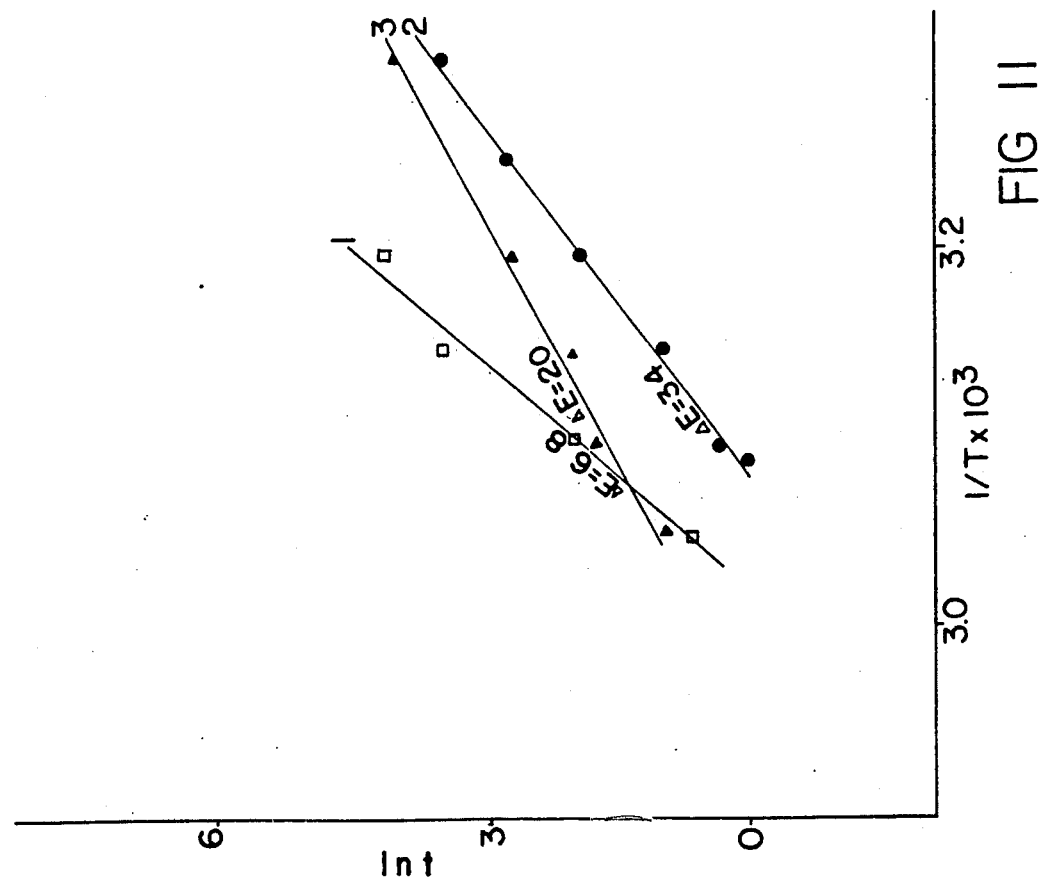

The indicator, pp4BCMU was incorporated into a synthetic elastomer and a mixture of two activators, triacetin and linoleic acid, was incorporated in silicone matrix. The Arrhenius plots for some of these systems are shown in FIG. 11. The effect of the mixture of activators on activation energy is presented in table 11. As can be seen from table 11, the activation energy can be varied from 20 to 68 kcal/mole by using mixtures of activators.

TABLE 11

Effect of activator mixtures on the activation energy. Concentrations of activators and indicators in the matrix are given in the parentheses.
SYSTEM:
Indicator Tape: Indicator: pp4BCMU, Concn.: 8%; Matrix: Elastomer
Activator Tape: Activator: Varied, Concn.: Varied; Matrix: Silicone

| Indicator System | | Activator System | | Activation Energy | Plot # in |
|---|---|---|---|---|---|
| Indicator | Matrix | Activator | Matrix | (kcal/mole) | FIG. 11 |
| pp4BCMU (8%) | Elastomer | LA (28%) | Silicone (3% catalyst) | 68 | 1 |
| pp4BCMU (8%) | Elastomer | TA + LA (22%) (1:1) | Silicone (3% catalyst) | 34 | 2 |
| pp4BCMU (8%) | Elastomer | TA (22%) | Silicone (3% catalyst) | 20 | 3 |

Notes:
See table 5 for the manufacturers of the adhesives and their properties. Unless specified, the concentration of catalyst for the silicone resin was 3%.
TA = Triacetin, LA = Linoleic acid, and pp4BCMU = Partially polymerized 4BCMU

EXAMPLE 7

Effect of Adhesive Tack on the Activation Energy

Figure 12:
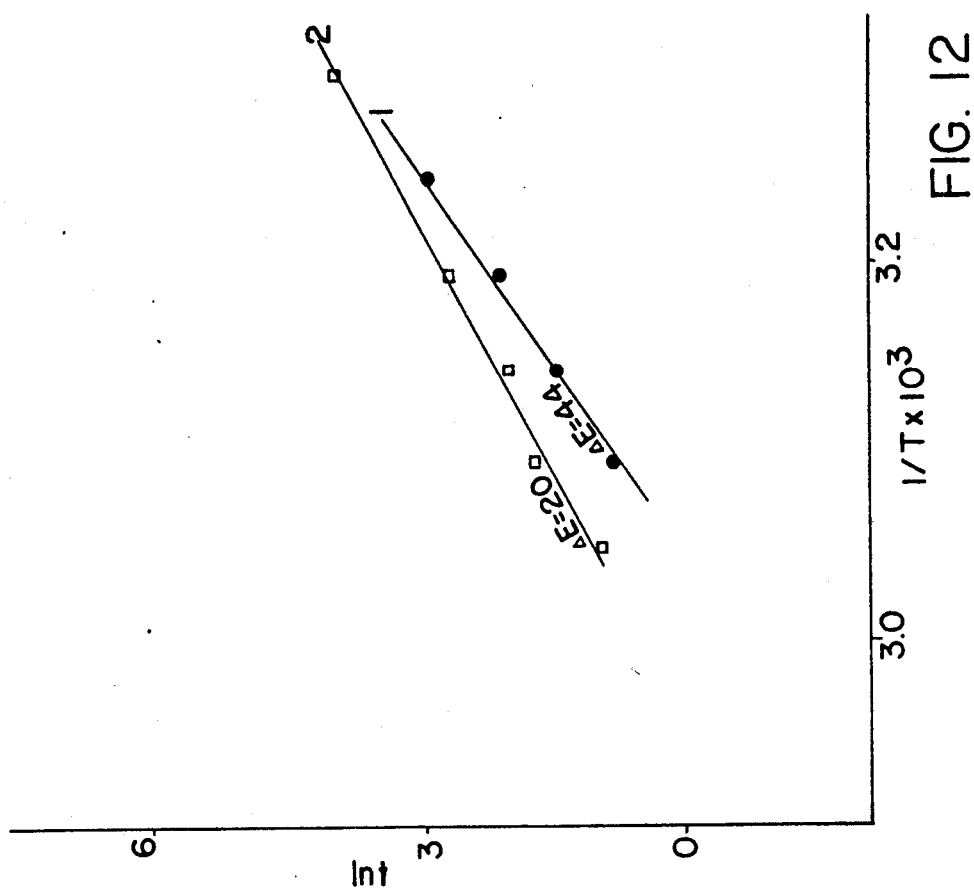

The tackiness (adhesive ability, formation of adhesive bond with a substrate) of some adhesives can be varied by adding a tackifier or a catalyst. The adhesive ability of silicone adhesives can be decreased to almost nonadhesive nature by adding certain proprietary catalysts which crosslink the adhesive. The catalyst for the silicone adhesive used herein was also supplied by the manufacturer. In order to study the effect of catalyst (which decreases the tackiness) on the activation energy, triacetin was incorporated in silicone adhesive containing different concentrations of the catalyst. The indicator, pp4BCMU was incorporated into a synthetic elastomer. The Arrhenius plots for these systems are shown in FIG. 12. The effect of concentration of the catalyst on the activation energy is presented in table 12. As can be seen, the activation energy can be varied from 44 to 20 kcal/mole by varying the tackiness (concentration of the catalyst from 0.6 to 3%) of the matrix.

TABLE 12

Effect of variation of adhesive tack on the activation energy. Concentrations of activators and indicators in the matrix are given in the parentheses.
SYSTEM:
Indicator Tape: Indicator: pp4BCMU, Concn.: 8%; Matrix: Elastomer
Activator Tape: Activator: Triacetin, Concn.: Varied; Matrix: Silicone

| Indicator System | | Activator System | | Activation Energy (kcal/mole) | Plot # in FIG. 12 |
|---|---|---|---|---|---|
| Indicator | Matrix | Activator | Matrix | | |
| pp4BCMU (8%) | Elastomer | TA (22%) | Silicone (0.6% Catalyst) | 44 | 1 |
| pp4BCMU (8%) | Elastomer | TA (22%) | Silicone (3% catalyst) | 20 | 2 |

Notes:
See table 5 for the manufacturers of the adhesives and their properties. Unless specified concentration of catalyst for the silicone resin was 3%.
TA = Triacetin, and pp4BCMU = Partially polymerized 4BCMU

SUMMARY OF THE ACTIVATION ENERGY RESULTS

Table 13 summaries the effects of different variables on the activation energy. As is seen, by varying the nature of activator and the matrix, one can vary the activation energy from 20 to 68 kcal/mole. Though selected variables were only studied over a limited range, it is evident that the device is extremely flexible. It is possible, utilizing the above methodology, to vary the time required for the color change, and the activation energy, for most TTM systems reported in the literature. For the pp4BCMU system, we have demonstrated that the activation energy can at least be varied from 20 to 68 kcal/mole. By selecting and varying the nature of the other parameters listed in table 4, the activation energy can be varied over very wide range, e.g. from 1 to 200 kcal/mole.

EXAMPLE 8

Variation in Time Required for the Color Change

During the activation energy study reported above, the time required for the color change was recorded. The time required for the initiation of the color change can be varied by several orders of magnitude by varying the parameters listed in table 4. A typical example is given in table 14, where the time required for the color change has been varied by over three orders of magnitude by varying the activator. Thus it is possible to vary the time required for the color change by several orders of magnitude.

TABLE 14

Time required for the color change for pp4BCMU system at 7° C.
SYSTEM:
Indicator Tape: Indicator: pp4BCMU, Concn.: 8%;

TABLE 13

Summary of the effect of variables on the activation energy of the 4BCMU device.
Concentrations of initiators and indicators in a particular matrix are given in parentheses.
SYSTEM:
Indicator Tape: Indicator: pp4BCMU, Concn.: Varied; Matrix: Varied
Activator Tape: Activator: Varied, Concn.: Varied; Matrix: Varied

| Indicator System | | Activator System | | Eact (kcal/mole) | Perishable having the same Eact, see page # in book by Labuza |
|---|---|---|---|---|---|
| Indicator | Matrix | Activator | Matrix | | |
| pp4BCMU (17%) | Elastomer | LA (28%) | Silicone | 68 | Asparagus p 334 |
| pp4BCMU (17%) | Silicone | TA (17%) | Silicone | 62 | |
| pp4BCMU (8%) | Elastomer | TA (22%) | Acrylate/TW | 50 | Snap bean p 334 |
| pp4BCMU (8%) | Elastomer | TA (22%) | Acrylate/NS | 45 | Raspberries p 337 |
| pp4BCMU (8%) | Elastomer | TA (22%) | Silicone (0.6% catalyst) | 44 | Strawberries p 337 |
| pp4BCMU (8%) | Elastomer | TA (22%) | Elastomer + Acrylate/TW (7:3) | 42 | Asparagus p 334 |
| pp4BCMU (8%) | Elastomer | TA (22%) | Elastomer + Acrylate/TW (3:7) | 40 | Peas p 335 |
| pp4BCMU (8%) | Elastomer | TA (22%) | Vinylacetate | 39 | Wheat p 90 |
| pp4BCMU (8%) | Elastomer | TA + LA (1:1) | Silicone | 34 | Broccoli p 335 |
| pp4BCMU (30%) | Acrylate | TA (22%) | Acrylate/TW | 34 | Broccoli p 335 |
| pp4BCMU (8%) | Elastomer | LA (28%) | Elastomer | 33 | Lima beans p 334 |
| pp4BCMU (8%) | Silicone | TA (31%) | Elastomer | 32 | Sweet corn p 253 |
| pp4BCMU (8%) | Elastomer | TA (31%) | Elastomer | 31 | Chicken p 155 |
| pp4BCMU (8%) | Elastomer | TA (22%) | Silicone + Elastomer (3:7) | 23 | Fish-Halibut p 185 |
| pp4BCMU (8%) | Elastomer | TA (22%) | Silicone | 20 | Milk p 201 |

Notes:
See table 5 for the manufacturers of the adhesives and their properties. Unless specified concentration of catalyst for the silicone resin was 3%.
Ea = Activation energy of the device, TA = Triacetin, LA = Linoleic acid, TW = Testworth Lab., NS = National Starch, and pp4BCMU = Partially polymerized 4BCMU.
Notes for the last column:
The perishables reported in this column are based on the activation energy reported in the book by Labuza. Page numbers are given for reference where the same data is listed after the perishable. Once the activation energy of the perishable is established, the shelf life of the perishable can be matched by varying the time required for the color change of the device using the techniques described in the following examples.

TABLE 14-continued

Matrix: Elastomer
Activator Tape: Activator: Varied, Concn.: Varied;
Matrix: Varied.

| Indicator System | | Activator System | | Color Initiation Time (in minutes and hours) |
|---|---|---|---|---|
| Indicator | Matrix | Activator | Matrix | |
| pp4BCMU (8%) | Elastomer | LA (22%) | Silicone | 10,200 min (170 hrs) |
| pp4BCMU (8%) | Elastomer | TB (31%) | Elastomer | 10 min (0.17 hr) |

Notes:
See table 5 for the manufacturers of the adhesives and their properties. Unless specified concentration of catalyst for the silicone resin was 3%.
TB = Tributarin, LA = Linoleic acid, and pp4BCMU = Partially polymerized 4BCMU

EXAMPLE 9

Use of Acids as Activators and pH Dyes as Indicators

A wide range of dyes which are sensitive to acids and bases are commercially available. One of the water insoluble dye (pentamethoxytriphenylmethane, PTM) undergoes a colorless to red color change when exposed to water insoluble acids such as benzoic acid. This type of dye/acid combination can provide a tape device which can be unaffected by moisture. The other dye, bromophenol blue sodium salt (BPB-Na) undergoes a series of color change, blue to green-blue to green to yellow-green to yellow to orange to red when exposed to acids such as citric acid and vitamin-C (L-ascorbic acid). This type of dyes can provide desirable visual colors e.g. green to yellow to red. These dyes were incorporated into different adhesives and used as the indicator tape. Organic acids, including citric acid, vitamin-C, benzoic acid, heptanoic, and adipic acids were incorporated into different adhesives and coated on Mylar film to produce the activator tape. The devices were activated by laminating the activator tape over the indicator tape.

An indicator tape was prepared by mixing 0.8 g of 2,2',4,4',4''-pentamethoxytriphenylmethanol (PTM) and 8 g of acrylic adhesive (Scotch Grip 4268, 3M Company) according to the procedure described in Method 3. An activator tape was prepared by mixing 2.0 g of citric acid and 9.8 g of vinyl acetate adhesive (J8905, United Resin, Inc.) according to the procedure described in Method 3. The devices were prepared (activated) by laminating the activator tape on to the indicator tape according to the procedure described in Method 4. Several such devices were annealed at different temperatures and the time required for initiation of the color change (colorless to red) was noted. The time required for the color change was 44, 38, 15, and 8 minutes at 60°, 70°, 80° and 90° C. The activation Energy determined from the Arrhenius plot was 13 kcal/mole. The results for the other systems, i.e., adipic acid, benzoic acid, and vitamin-C as activators and pentamethoxytrimethoxy methanol and bromophenol blue —sodium salt as indicators using different adhesives as the matrix, are summarized in table 15.

TABLE 15

Activation energy of pH sensitive systems having citric acid and sodium carbonate as an activator combination. Concentration of activators and indicators are presented in parentheses:
SYSTEM:
Indicator Tape: Indicator: Varied, Concn.: Varied; Matrix: Varied
Activator Tape: Activator: Varied, Concn.: Varied; Matrix: Varied

| Indicator System | | Activator System | | Activation Energy |
|---|---|---|---|---|
| Indicator | Matrix | Activator | Matrix | (kcal/mole) |
| BPB—Na (2%) | Syn. Latex | Citric acid (3%) | Vinylacetate | 20 |
| BPB—Na (2%) + SC (0.5%) | " | " | " | 24 |
| BPB—Na (2%) | " | Citric acid (16%) | Elastomer | 20 |
| BPB—Na (2%) + SC (0.5%) | " | " | " | 22 |
| PTM (2%) | Elastomer | Citric acid (3%) | " | 15 |
| PTM (2%) | Acrylate | " | Vinylacetate | 13 |
| BPB (3%) | Vinylacetate | SC (4%) | " | 10 |
| BPB (3%) | PVC/Acrylate | SC (5%) | Syn Latex | 20 |

Notes:
See table 5 for the manufacturers of the adhesives and their properties. Unless specified concentration of catalyst for the silicone resin was 3%.
BPB—Na = Bromophenol blue sodium salt BPB = Bromophenol blue, PTM = Pentamethoxytriphenylmethane, and SC = Sodium carbonate.

Comparing the activation energy results summarized in table 13, where the activators of relatively low polarity compounds were used, with those reported in table 15, where the activators have higher polarity, it is seen that for the same adhesive matrices, the activation energy is lower when the polarity of the activator is increased. This effect becomes more apparent in examples 13 and 14, where highly polar (highly ionizable) inorganic compounds are used as the activators.

EXAMPLE 10

Induction Period

In addition to the parameters described in Table 4, there are several other parameters such as incorporation of activator-reactive additives in the indicator matrix that can also increase the induction period. For example, citric acid reacts with sodium carbonate, a simple acid/base reaction. The reaction between sodium carbonate and citric acid can not be seen because it is not associated with color change. If sodium carbonate is also incorporated in to the indicator matrix, citric acid diffusing into the indicator matrix will first react with (be consumed by) sodium carbonate. Once all sodium carbonate is consumed, citric acid then will react with the dye to introduce color change. Thus, it will require a longer time to see the color change. The induction period will depend upon the concentration of the reactive additive. The induction period will increase with increase in concentration of the additive. Thus the induction period can be increased without changing the activation energy.

We have observed that if the concentration of citric acid is significantly high, i.e., more than 50%, it will crystallize out of the matrix and will not migrate to the indicator layer to introduce a color change.

Two indicator tapes were prepared from synthetic latex (40-0033, United Resin) one containing 2% of bromophenol blue and other containing 2% of bromophenol blue plus 0.5% sodium carbonate according to the procedure described in Method 3. An activator tape was prepared from vinyl acetate adhesive (J8905, United Resin, Inc.) containing 2% citric acid according to the procedure described in Method 3. The devices were prepared (activated) by laminating the activator tape on to the indicator tapes according to procedure described in Method 4. The time required for initiation of blue to yellow color change was noted. The device containing bromophenol blue required 480 minutes while that containing bromophenol blue plus sodium carbonate required 840 minutes for the blue to yellow color change. The results for the other systems are summarized in table 16.

TABLE 16

Effect of thickness and additives on time required for color change at 90° C.
Concentration of activator and indicator is presented in parentheses.
SYSTEM:
Indicator Tape: Indicator: Varied, Concn.: Varied; Matrix: Varied
Activator Tape: Activator: Varied, Concn.: Varied; Matrix: Varied

| Indicator System | | Activator System | | Time for color |
|---|---|---|---|---|
| Indicator | Matrix | Activator | Matrix | Change (min) |
| PTM (2%) | Elastomer | Citric acid (16%) | Elastomer | 2 |
| PTM (2%) | Acrylate | Citric acid (2%) | Vinylacetate | 8 |
| BPB—Na (2%) | Syn Latex | " | " | 480 |
| BPB—Na (2%) + SC (0.5%) | " | " | " | 840 |
| BPB—Na (2%) | " | Citric acid (16%) | Elastomer | 860 |
| BPB—Na (2%) + SC (0.5%) | " | " | " | 1800 |

Notes:
See table 5 for the manufacturers of the adhesives and their properties. Unless specified concentration of catalyst for the silicone resin was 3%.
PTM = Pentamethoxytriphenylmethane, BPB—Na = Bromophenol blue sodium salt, SC = Sodium carbonate

EXAMPLE 11

Use of an Oxidant as Activator and Redox Dye as Indicator

An indicator tape was prepared from elastomeric adhesive (4910 3M Company) containing 7% of leucomalachite green as a reduced dye according to the procedure described in Method 3. An activator tape was prepared from vinyl acetate adhesive (J8905, United Resin, Inc.) containing 4% ammonium persulfate as an oxidant according to the procedure described in Method 3. The device was prepared (activated) by laminating the activator tape onto the indicator tape according to the procedure described in Method 4. The assembled tape was cut into several smaller devices which were annealed in the temperature range of 35 to 75 degrees centigrade and the time required for initiation of color change (colorless to green) was noted. For example, one device, annealed at 35+ C. required 66 minutes, and another device annealed at 75° C. required 4 minutes. The activation Energy determined from the Arrhenius plot was 24 kcal/mole. The results are summarized in table 17.

TABLE 17

Activation energy of oxidizing and reducing systems. Concentration of activator and indicator is presented in parentheses.
SYSTEM:
Indicator Tape: Indicator: Varied, Concn.: Varied; Matrix: Varied
Activator Tape: Activator: Varied, Concn.: Varied; Matrix: Varied

| Indicator System | | Activator System | | Activation Energy |
|---|---|---|---|---|
| Indicator | Matrix | Activator | Matrix | (kcal/mole) |

TABLE 17-continued

| LeucoMG (7%) | Elastomer | AP (4%) | Vinylacetate | 24 |
|---|---|---|---|---|
| MG (0.5) | " | SS (2%) | " | 24 |

Notes:
See table 5 for the manufacturers of the adhesives and their properties. Unless otherwise specified, the concentration of catalyst for the silicone resin was 3%.
LeucoMG = Leuco malachite green, MG = Malachite green, APS = Ammonium persulfate, and SS = Sodium sulfite.

EXAMPLE 12

A Reducing agent as an Activator and a Redox Dye as an Indicator

An indicator tape was prepared from an elastomeric adhesive (4910 3M Company) containing 0.5% of malachite green as an oxidized dye according to the procedure described in Method 3. An activator tape was prepared from vinyl acetate adhesive (J8905, United Resin, Inc.) containing 2% of sodium sulfide as a reducing agent according to the procedure described in Method 3. The device was prepared (activated) by laminating the activator tape on to the indicator tape according to procedure described in Method 4. The assembled tape was cut into several smaller devices and were annealed in a temperature range of 70-90 degrees centigrade, and the time required for initiation of color change (green to colorless) was noted. For example, one device, annealed at 70° C. required 165 hours, while another device, annealed at 90° C. required 22 hours. The activation Energy determined from the Arrhenius plot was 24 kcal/mole. The results are summarized above in Table 17.

EXAMPLE 13

Cation as an Activator

An indicator tape was prepared by mixing 100 mg of 2,2'-bipyridyl and 10 g of synthetic elastomer (4910, 3M Company) according to the procedure described in Method 3. An activator tape was prepared by mixing 500 mg of ferrous sulfate and 10 g of vinyl acetate (United Resin J8905) according to the procedure described in Method 3. The device was prepared (activated) by laminating the activator tape onto the indicator tape according to procedure described in Method 4. Two devices, thus made, were annealed at 25°, 50°, and 74° C. and the time required for initiation of color change (colorless to red) was 20, 13 and 10 minutes, respectively. The Eact of the device was 2.9 kcal/mole.

The activation energy of this system is so low that it can be used essentially for monitoring time. The effect of temperature is almost negligible.

EXAMPLE 14

Anion as an Activator

An indicator tape was prepared by mixing 200 mg of ferric chloride, 1 g water and 10 g of vinyl acetate (United Resin J8905) according to the procedure described in Method 3. An activator tape was prepared by mixing 500 mg of sodium thiocyanate, 1 g water and 10 g of vinyl acetate (United Resin J8905) according to the procedure described in Method 3. The device was prepared (activated) by laminating the activator tape on to the indicator tape according to procedure described in Method 4. Two devices, made thus, were annealed at 25°, 50°, and 70° C. and the time required for initiation of color change (brown to red) was 30, 20, and 15 minutes, respectively. The Eact of the device was 3.1 kcal/mole. The activation energy of this system is so low that it can be used essentially for monitoring time. The effect of temperature is almost negligible.

It can be seen from results summarized in tables 13 and 15, and examples 13 and 14 that the Eact can be decreased by increasing the difference in polarity (or ionization) of the activator and the matrix. For example, when a nonpolar elastomer is used as a matrix for activator, the Eact is usually higher than 30 kcal/mole for nonionizable/nonpolar organic activator (table 13), the Eact is higher than 15 kcal/mole for polar/ionizable organic compounds such as citric acid (table 15), and the Eact is less than 10 kacl/mole for ionic activator (examples 13 and 14).

EXAMPLE 15

Change in Fluorescence

An indicator tape was prepared by mixing 200 mg of 8-hydroxyquinoline and 10 g of synthetic elastomer (Scotch-Grip 4910, 3M) using the procedure described in Method 3. This coating was done on polyethylene substrates. An activator tape was prepared by mixing 500 mg of magnesium chloride, 1 g water and 9 g of vinyl acetate (United Resin J8905) using the procedure described in Method 3. The device was prepared (activated) by laminating the activator tape on to the indicator tape according to procedure described in Method 4. The device was kept at 80° C. for 2 hrs and checked for fluorescence under short wavelength UV at 254 nm. The device, which did not fluoresce at the time of activation, showed a bluish fluorescence under UV light after the annealing.

EXAMPLE 16

Message Device

An activator tape was prepared by coating a mixture of 0.5 g citric acid and 10 g synthetic Elastomer (Scotch Grip 4914, 3M Company) as described in Method 3. An indicator tape was prepared by writing the following message with an ink (mixture of pentamethoxytriphenyl methanol and polyvinylchloride in tetrahydrofuran) on a polyester sheet:

"IF RED, DO NOT USE".

The device was prepared (activated) by laminating the activator tape onto the indicator tape according to procedure described in Method 4. The colorless message became red in color within one hour at room temperature.

EXAMPLE 17

Production of Activator by Thermal Decomposition in the Assembled Device

An indicator tape was prepared by mixing 100 mg of bromophenol blue and 10 g of synthetic elastomer (4910, 3M Company) according to the procedure described in Method 3. An activator tape was prepared by mixing 1 g of ammonium carbonate and 10 g of vinyl acetate (United Resin J8905) according to the procedure described in Method 3. The device was prepared (activated) by laminating the activator tape on to the indicator tape according to procedure described in Method 4. The assembled tape was cut into several smaller devices and were annealed in the temperature range 50° to 90° C., and the time required for initiation of color change was noted. The device annealed at 50° C. turned green after 20 minutes; the one annealed at 70° C. in 7 min.; the one at 80° C. in 5 min.; the one at 90° C. in 3 min.; and the one at room temperature after 1 hour.

EXAMPLE 18

Production of Activator by UV Irradiation of Assembled Device

An indicator tape was prepared by mixing 1 g of triphenyl sulfonium hexafluoroantimonate and 10 g of acrylic adhesive (Durotech 80-1068, National Starch) using the procedure described in Method 3. This coating was done on 4 mil polyethylene film. An activator tape was prepared by mixing 100 mg of pentamethoxytriphenyl methanol and 10 g of acrylic (Duro-Tak 80-1068) using the procedure described in Method 3. The device was assembled by laminating the activator tape on to the indicator tape according to procedure described in Method 4. The device did not change color when protected from UV light. The laminated device was activated by exposing to a short wavelength UV light through the polyethylene substrate for a minute. Upon UV irradiation, the activator, triphenyl sulfonium hexafluoroantimonate produced an acid. The device still did not change color. The device changed to pink after 12 hours and red after 30 hours at room temperature. A similarly prepared unirradiated device did not change color under similar conditions after two months exposure at room temperature.

EXAMPLE 19

Change in Conductivity

A flexible printed circuit board (EZ Circuit, EZ 1334, Bishop Graphics Inc., Westlake Village, Calif.) having parallel conductive stripes was coated with 1,6 dichloro-2,4-hexadiyne (referred hereafter to as 1C) to see experimentally if a conductivity change could be detected under the predetermined conditions. The resulting device was cooled to $-20°$ C. and exposed to a short wavelength UV lamp for ten minutes for polymerization of 1C. The device was connected to an electrometer (Kiethley Model 617). The device had an electrical resistance of $1.61 \times 10^{12}$ ohms. The device was then activated by applying an adhesive tape (synthetic elastomer (Scotch Grip, 4914, 3M Company) containing pyridine. The decrease in electrical resistance was determined with time at room temperature. The resistivity was $3.3 \times 10^{10}$ and $0.8 \times 10^7$ ohms after 2 and 8 hours respectively. The device also turned colorless to dark (essentially brown-black at the end of the experiment) simultaneously with the measured changes in the conductivity.

EXAMPLE 20

Bar Coded Device

Bar coding is currently used commercially to track inventory in warehouses and to read prices of foods in supermarkets. Supermarket's Universal Product Code System is different from the industrial bar coding system. The Industrial bar code system can monitor manufacturing processes, warehouse inventories, hospital supplies, library books, office records, while the supermarket bar coding is used for both the purposes, including monitoring inventory and reading package prices at store check out counters. In most supermarkets in the USA, the prices of foods are read by a bar code reader from the prices printed in form of bar codes on the containers. In order to demonstrate that the shelf life monitoring devices can also be prepared in form of bar codes, two type of bar coded adhesive tape devices were prepared.

One gram of 4BCMU was dissolved in a mixture of 5 g of chloroform and 4 g of acrylic adhesive (Testworth Laboratory) to see experimentally if the device could be used as a bar code indicator. The resulting mixture was coated on a Mylar polyester film using the procedure described in Method 3. A mask (negative) of a bar code was prepared by copying it on a transparent cellophane film in a copying machine. The mask of the bar code was placed on the 4BCMU coating and exposed to short wavelength UV light to get the impression of the bar code in blue color (partially polymerized 4BCMU). The cellophane mask was then removed. The bar coded 4BCMU is the indicator tape. An activator tape comprising of triacetin in the acrylic adhesive was prepared according to the procedure described in Method 5. The device was activated according to the procedure described in Method 4. The device was placed in an oven at 40° C. After about two hours the blue bars of the device started turning red and at three hours, the bars were red. Though 4BCMU was used to demonstrate the concept, one can print the desired information in the form of bar codes with any of the indicators and activators described herein and formulated into an appropriate activator tape.

EXAMPLE 21

A Different Method of Creating the Bar Coded Tape Device

An indicator tape consisting of bromophenol blue in a synthetic elastomer (3M #4914) was coated on a Mylar polyester film using an applicator of cut depth 0.006". Subsequently an applicator of cut depth 0.0015% wound around with a nylon thread in a regular pattern was moved across the above coating creating lines which function as bars and spaces. When this indicator tape was brought in contact with a sodium carbonate activator tape, the color of the indicator changed from yellow to green in about 2 hours and then to blue in 12 hours. Thus bar codes can be created by scratching the indicator tape.

The bar code readers can read blue or black colors only. If pp4BCMU is used, the reader would not be able to read the code (the shelf life) and send a programmed signal to reject the product. In case of bromophenol blue, the reader can be programmed to reject the product if it can read the code. Thus the system can be totally automated. The bar code readers will read the information on the product and its shelf life simultaneously and print on the purchase receipt. As most major supermarkets are equipped with bar code readers, no additional equipment will be required.

A barrier matrix layer can also be utilized in the bar code device to introduce an induction period and also to alter the Eact of the color-indicating system.

What is claimed is:

1. A device for measuring the shelf life of a perishable product having a measurable activavation energy of product deterioration comprising:
   a) an indicator tape comprised of a transparent polymer film and affixed thereto at least one matrix layer containing an indicator composition:
   b) an activator tape comprised of a substrate and affixed thereto at least one matrix layer containing an activator composition:
   c) a composite matrix, comprised of said indicator tape and activator tape matrix layers, bonded together by at least one water-impermeable pressure sensitive adhesive, said activator composition being capable of diffusing through said composite matrix in a predetermined time to contact and chemically react with said indicator composition producing a visually observable color change in said indicator composition, said device being substantially impermeable to moisture, and said device possessing an activation energy and rate constant for color change which are substantially the same as the activation energy and rate constant for product deterioration of the perishable product in the temperature region of monitoring.

2. The device of claim 1 wherein said composite matrix further comprises at least one barrier matrix layer permeable to said activator composition, laminated to said activator and indicator matrix layers.

3. The device of claim 1 wherein said polymer film is comprised of polyethylene, polypropylene, polyester, polyurethane, polyamide, polyvinylchloride, polycarbonate or cellulose acetate.

4. The device of claim 1 wherein said substrate is a translucent or opaque polymer film or metal foil.

5. The device of claim 1 wherein said indicator, activator or barrier matrix is independently a resin of the type: epoxy, phenol-formaldehyde, amino-formaldehyde, polyamide, vinyl, acrylic, polyurethane, polyester, alkyd, synthetic elastomer rosin, or pressure sensitive adhesive.

6. The device of claim 1 wherein said activator is an oxidizing agent and said indicator is redox dye.

7. The device of claim 1 wherein said activator is a reducing agent and said indicator is a redox dye.

8. The device of claim 1 wherein said activator is a base and said indicator is a base sensitive pH dye.

9. The device of claim 1 wherein said activator is an acid and said indicator is an acid sensitive pH dye.

10. The device of claim 9 where in said activator is citric acid and said indicator dye is 2,2',4,4',4''-pentamethoxy triphenylmethanol.

11. The device of claim 1 wherein:
   a.) the indicator tape comprises: a polyester film, a synthetic elastomer matrix containing 2,2',4,4',4''-pentamethoxy triphenylmethanol;

b.) the activator tape comprises: a polyester film, the same synthetic elastomer as in (a) and containing and citric acid in solid solution.

12. The device of claim 1 wherein said indicator composition is displayed as at least one alphanumeric figure.

13. The device of claim 1 wherein said indicator composition is displayed as at least one bar code.

14. A process for monitoring the time-temperature storage history of a perishable product comprising the step of affixing to said product the device according to claim 1, and activating the device.

15. The process of claim 14 wherein the activating is by thermal annealing.

16. The process of claim 14 wherein the activating is by radiation.

17. The process of claim 14 wherein the activating is by applying pressure.

18. A perishable product having the device of claim 1, in activated form, attached thereto.

* * * * *